(12) United States Patent
Cichy et al.

(10) Patent No.: US 11,980,881 B2
(45) Date of Patent: *May 14, 2024

(54) PURGEABLE PHARMACEUTICAL FILL NEEDLE

(71) Applicant: VANRX PHARMASYSTEMS INC., Burnaby (CA)

(72) Inventors: Marcin Cichy, Surrey (CA); Juvenal Naing, Belcarra (CA); Carlos Alberto Diaz Guerrero, Burnaby (CA)

(73) Assignee: VANRX PHARMASYSTEMS INC., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/887,667

(22) Filed: Aug. 15, 2022

(65) Prior Publication Data
US 2022/0387988 A1  Dec. 8, 2022

Related U.S. Application Data

(62) Division of application No. 16/858,599, filed on Apr. 25, 2020, now Pat. No. 11,439,999.

(51) Int. Cl.
*B01L 1/02* (2006.01)
*A61J 1/12* (2006.01)
(Continued)

(52) U.S. Cl.
CPC ............. *B01L 1/025* (2013.01); *A61J 1/12* (2013.01); *A61J 1/14* (2013.01); *A61J 1/20* (2013.01);
(Continued)

(58) Field of Classification Search
CPC .... B01L 1/025; B01L 1/04; B01L 3/02; B01L 3/0293; B01L 2200/026; B01L 2200/0689;
(Continued)

(56) References Cited

U.S. PATENT DOCUMENTS 2,509,756 A    5/1950  Berthelsen
5,021,049 A *  6/1991  Howard .............. A61M 5/3213
                                                604/263
(Continued)

FOREIGN PATENT DOCUMENTS

CN    108473215 A    8/2018
CN    108542770 A    9/2018
(Continued)

OTHER PUBLICATIONS

China National Intellectual Property Administration Office Action and Search Report (for Chinese national stage of PCT/CA2019/051524), corresponding to the subject matter of the present application, dated Sep. 2, 2022.
(Continued)

*Primary Examiner* — Michael L Hobbs
(74) *Attorney, Agent, or Firm* — Brannon Sowers & Cracraft PC; Kevin R. Erdman

(57) ABSTRACT

The present invention involves a fill needle system for aseptically dispensing a pharmaceutical fluid in an aseptic chamber comprises a fill needle tubing in fluid communication with a pharmaceutical fluid source via flexible tubing and extending through a fill needle hub; a fill needle dispensing tip disposed at a dispensing end of the fill needle tubing; a fill needle sheath shaped and arranged to removably mate with and seal aseptically to the fill needle hub to form an aseptically sealed volume enclosing the dispensing tip; and a fluid pressure pulse induction system disposed and configured to compress the flexible tubing in order to dislodge droplets of pharmaceutical fluid retained on the dispensing tip after halting dispensing of the pharmaceutical fluid. An associated method of dispensing pharmaceutical fluid comprises operating the fluid pressure pulse induction system to dislodge the droplets. The system may comprise a (Continued)

controller for automatically controlling the dispensing and droplet dislodging.

21 Claims, 29 Drawing Sheets

(51) Int. Cl.

| | | |
|---|---|---|
| A61J 1/14 | (2023.01) | |
| A61J 1/20 | (2006.01) | |
| A61L 2/07 | (2006.01) | |
| A61L 2/16 | (2006.01) | |
| A61L 2/24 | (2006.01) | |
| B01L 1/04 | (2006.01) | |
| B01L 3/02 | (2006.01) | |
| B25J 21/00 | (2006.01) | |
| B65B 3/00 | (2006.01) | |
| B65B 3/04 | (2006.01) | |
| B65B 55/12 | (2006.01) | |
| C12M 1/00 | (2006.01) | |
| C12M 1/12 | (2006.01) | |
| G01N 35/00 | (2006.01) | |
| G01N 35/10 | (2006.01) | |

(52) U.S. Cl.
CPC .................................. *A61L 2/07* (2013.01); *A61L 2/16* (2013.01); *A61L 2/24* (2013.01); *B01L 1/04* (2013.01); *B01L 3/02* (2013.01); *B25J 21/00* (2013.01); *B65B 3/003* (2013.01); *B65B 3/04* (2013.01); *B65B 55/12* (2013.01); *C12M 29/00* (2013.01); *C12M 37/02* (2013.01); *C12M 41/14* (2013.01); *G01N 35/00029* (2013.01); *G01N 35/10* (2013.01); *B01L 2200/026* (2013.01); *B01L 2200/0689* (2013.01); *B01L 2200/141* (2013.01); *B01L 2300/0609* (2013.01); *B01L 2300/0832* (2013.01); *B01L 2400/0487* (2013.01); *G01N 2035/00148* (2013.01); *G01N 2035/00277* (2013.01); *G01N 35/0099* (2013.01)

(58) Field of Classification Search
CPC ....... B01L 2200/141; B01L 2300/0832; B01L 2400/0487; B65B 3/003; B65B 3/04; B65B 55/12; B65B 55/027; A61J 1/12; A61J 1/14; A61J 1/20; A61L 2/07; A61L 2/16; A61L 2/24; C12M 29/00; C12M 37/02; C12M 41/14; G01N 35/00029; G01N 35/10; G01N 35/0099; G01N 2035/00148; G01N 2035/00277; G01F 15/007

See application file for complete search history.

(56) References Cited

U.S. PATENT DOCUMENTS

| | | |
|---|---|---|
| 6,296,811 B1 * | 10/2001 | Sasaki ............... G01N 35/1065 310/326 |
| 6,957,781 B2 | 10/2005 | Gowens et al. |
| 9,993,815 B2 | 6/2018 | Immerzeel et al. |
| 11,014,696 B2 * | 5/2021 | Diaz Guerrero ........ B65B 43/60 |
| 2005/0056707 A1 | 3/2005 | Gowens |
| 2006/0008507 A1 | 1/2006 | Gore |
| 2009/0298129 A1 | 12/2009 | Spence |
| 2016/0346777 A1 | 12/2016 | Immerzeel |
| 2018/0282008 A1 | 10/2018 | Diaz Guerrero |
| 2019/0016484 A1 | 1/2019 | Diaz Guerrero |

FOREIGN PATENT DOCUMENTS

| | | |
|---|---|---|
| CN | 108602571 A | 9/2018 |
| TW | 201808560 A | 3/2018 |
| WO | 20190055030 A1 | 3/2019 |

OTHER PUBLICATIONS

Canadian Intellectual Property Office International Search Report (PCT/CA2019/051524), corresponding to the subject matter of the present application, dated Feb. 4, 2020.
Canadian Intellectual Property Office International Written Opinion (PCT/CA2019/051524), corresponding to the subject matter of the present application, dated Feb. 4, 2020.
United States Patent and Trademark Office Non-Final Office Action (U.S. Appl. No. 16/858,599, filed Apr. 25, 2020), corresponding to the subject matter of the present application, dated Feb. 4, 2022.

* cited by examiner

PURGEABLE PHARMACEUTICAL FILL NEEDLE

CROSS-REFERENCE TO RELATED APPLICATIONS

The present application is a divisional of U.S. patent application Ser. No. 16/858,599, filed Apr. 25, 2020, now U.S. Pat. No. 11,439,999, issued on Sep. 13, 2022; which is a divisional of U.S. patent application Ser. No. 16/185,035, filed Nov. 18, 2018, now U.S Pat. No. 11,103,866, issued on Aug. 31, 2021. The subject matter of this application relates to that disclosed in U.S. patent application Ser. No. 14/890,223, filed Jul. 22, 2011, now U.S. Pat. No. 9,993,815, issued Jun. 12, 2018; which is a U.S. National Phase Entry of PCT Application No. PCT/US2012/047765, filed Jul. 20, 2012, which claims priority to provisional application 61/510,780, filed Jul. 22, 2011. This application also relates to that disclosed in U.S. patent application Ser. No. 15/375,019, filed Dec. 9, 2016, now U.S. Pat. No. 10,067,151, issued on Sep. 4, 2018; which claims priority to provisional application Ser. No. 62/265,938, filed Dec. 10, 2015. This application is a continuation-in-part of PCT International Patent Application No. PCT/CA2017/051071, filed Sep. 12, 2017, which claims priority to U.S. patent application Ser. No. 15/647,633, filed Jul. 12, 2017, now U.S. Pat. No. 10,710,758, issued Jul. 14, 2020; U.S. patent application Ser. No. 15/465,516, filed Mar. 21, 2017, now U.S. Pat. No. 10,524,980, issued on Jan. 7, 2020; and U.S. patent application Ser. No. 15/264,554, filed Sep. 13, 2016. This application is also a continuation-in-part of U.S. patent application Ser. No. 15/729,655, filed Oct. 10, 2017, now U.S. Pat. No. 10,723,497, issued Jul. 28, 2020. The disclosures of all of these applications are herein incorporated by reference herein.

TECHNICAL FIELD

This present invention relates to the medical field as exemplified by IPC class A61 and more particularly to apparatus and associated methods for sterilization of and sterile handling of pharmaceutical materials and containers for pharmaceuticals, including bringing pharmaceuticals into form for administration to medical or veterinary patients. In one aspect, it relates to the programmed and automatic operation of such apparatus configured and arranged for filling pharmaceutical containers with predetermined amounts of liquid or other materials.

BACKGROUND

Controlled environment enclosures are known in the art. Such enclosures are used, for example, for containment of hazardous materials. In other examples controlled environment enclosures are used to provide controlled environments with limited numbers of particulates.

In the art controlled environment enclosures are typically fitted with ports for transfer of materials in and out of the enclosure and the ports are fitted with gloves for manual manipulation of equipment, parts or materials inside the enclosure. Such gloves are subject to significant risk of puncture.

In some examples known in the art the controlled environment enclosure is also used to limit exposure to viable particulates. Such controlled environment enclosures may be required for aseptic processing of cell cultures and for the manufacture of pharmaceutical products, medical devices, food or food ingredients. In these cases it is a requirement that the controlled environment enclosure be decontaminated. This may be done thermally using steam or chemically using chemical agents. Suitable chemical agents known in the art include hydrogen peroxide, ozone, beta-propiolactone, aziridine, formaldehyde, chlorine dioxide, ethylene oxide, propylene oxide, and peracetic acid. In most cases the decontamination and sterilization operations have to be preceded by a cleaning process. Such cleaning processes have the function of removing major contamination by simple mechanical and chemical action.

In some examples in the prior art the controlled environment also contains automated equipment. Such automated equipment includes machines for filling of vials. The automated equipment located in the controlled environment is typically of such a size and complexity that it cannot be operated fully automatically without human intervention. Such human intervention typically requires the use of gloves with the associated risk of puncture.

Fluid paths within the controlled environment enclosures may be made from flexible tubing materials and may therefore have significant gas permeability. Gases that naturally occur in air, such as oxygen and carbon dioxide, as well as chemical decontamination agents are known to diffuse into these tubing materials. Accumulation of these agents in flexible tubing and subsequent delayed release may be a major contamination problem during operation. This applies in particular to products or solutions that are sensitive to exposure to alkylating agents, oxidizers, radicals or carbon dioxide. A typical example of human intervention involving the use of gloves is the installation of the fluid path or multiple fluid paths after the completion of decontamination.

In view of the above there remains a need for controlled environments that do not require human intervention via the use of gloves and in which pharmaceutical fluids may be accurately and aseptically dispensed into containers. In the present era of very expensive pharmaceuticals, designer drugs, and customized gene therapy preparations, it has become extremely important to aseptically dispense pharmaceutical fluids at very precise volumes into pharmaceutical containers. This is made all the more important by the fact that these pharmaceuticals are very expensive and are often provided in small volumes. At such low volumes, the amounts of pharmaceutical fluid retained in fill needles at the end of dispensing cycles may be a significant fraction of the total dispensed amount, and the same is true of unreleased droplets of fluid remaining pendant at the tip of the fill needle.

SUMMARY OF THE INVENTION

In one aspect of the invention there is provided a method for installing a fluid path within a controlled environment enclosure comprising, protecting the fluid path against an environment external to the fluid path; introducing the fluid path into the controlled environment enclosure; decontaminating the controlled environment enclosure; and mechanically unprotecting the fluid path within the controlled environment enclosure. The mechanically unprotecting may be by a robotic arm manipulation system. The decontaminating the controlled environment enclosure is automatically done after the introducing the fluid path into the controlled environment enclosure. The unprotecting is automatically done after the decontaminating the controlled environment enclosure.

In one aspect of the invention there is provided a method for transferring within a controlled environment enclosure a fluid along a fluid path to a destination within the controlled environment enclosure, comprising protecting the fluid path against an environment external to the fluid path; introducing the fluid path into the controlled environment enclosure; decontaminating the controlled environment enclosure; mechanically unprotecting the fluid path within the controlled environment enclosure; and transferring the fluid to the destination along the fluid path. The mechanically unprotecting may be by a robotic arm manipulation system. The fluid path may comprise a pre-sterilized tube. The method may further comprise filtering the fluid in the fluid path and the filtering may be sterile filtering. The destination may be at least one of a culture of cells, a culture of tissue, an enzyme solution, a suspension of immobilized enzymes, a mix of active ingredients, and an excipient. The fluid may be an aseptic fluid. The controlled environment enclosure may be an isolator. The destination may be microwell plates or containers for pharmaceutical products.

In one aspect of the invention there is provided a method for uninstalling a fluid path from a controlled environment enclosure, comprising mechanically protecting the fluid path within the controlled environment enclosure; decontaminating the controlled environment enclosure; opening the controlled environment enclosure; and removing the fluid path from the controlled environment enclosure. The mechanically protecting may be by a robotic arm manipulation system. The decontaminating the controlled environment enclosure may be done automatically after the protecting the fluid path. The opening the controlled environment enclosure may be done automatically after the decontaminating the controlled environment enclosure.

In one aspect of the invention there is provided a method for decontaminating a controlled environment enclosure having a fluid path, the method comprising mechanically protecting by a robotic action the fluid path within the controlled environment enclosure; decontaminating the controlled environment enclosure; and opening and closing the controlled environment enclosure. The opening and closing the controlled environment enclosure may be done before or after the decontaminating the controlled environment enclosure. The mechanically protecting may be by a robotic arm manipulation system. The decontaminating the controlled environment enclosure may be done automatically after the mechanically protecting the fluid path.

In one aspect of the invention there is provided an apparatus for protection and unprotection of a fluid path within a controlled environment enclosure that includes a fluid path terminated by a fill needle with removable sheath, and a remotely operated manipulation system for protection and/or unprotection of the fluid path. The remotely operated manipulation system may include a robotic arm manipulation system. The apparatus may further include a tamper-evident device positioned to reveal a breach of seal between the sheath and the fill needle. The apparatus may further include a removal station that includes a surface operative to interact with part of the sheath. The remotely operated manipulation system may include a robot end tool including at least one surface that is shaped to hold the fill needle. The fluid path may be a pre-sterilized unit.

In one aspect of the invention there is provided an apparatus for installing a fluid path within a controlled environment enclosure that includes means for conveying the fluid, and remotely operated means for protecting and/or unprotecting the means for conveying the fluid.

The inventors envision that compact and well-designed automated equipment may be operated inside closed controlled environments without the use of any gloves, eliminating thereby the risk of leaky gloves. The invention provides a method of installing a fluid path inside a controlled environment enclosure without the use of gloves. This requires the fluid path to be protected during the decontamination process and to be unprotected prior to the use of the fluid path. Furthermore, the fluid path may be automatically closed after use.

The closed fluid path may be re-opened and re-used at a later time. This may be useful for continuing the use of the fluid path after unplanned events that require breaking of the integrity of the enclosed controlled environment. Additionally, the closing of the fluid path may be particularly useful in situations where the fluid path has been in use for transfer of hazardous substances. After closing of the fluid path, the enclosed environment may be cleaned and decontaminated; after which the fluid path may be removed.

In a first aspect of the invention a fluid handling assembly is provided for automatically carrying out a fluid handling process in an aseptic environment, the assembly comprising a first sheath portion including an implement portion disposed within the first sheath portion for use in the process, a first locking mechanism portion, and a first sealing portion; a second sheath portion including a second locking mechanism portion configured to mate with positive detent with the first locking mechanism portion, and a second sealing portion disposed to aseptically seal with the first sealing portion when the first and second locking mechanism portions are mutually mated, wherein the first and second sheath portions define a sealed cavity that aseptically encapsulates the implement portion when the first and second locking mechanism portions are mutually mated. The assembly may be a fill assembly and the implement portion comprises a proximal dispensing portion of a fill needle, the fill needle including a fluid conduit that extends through the first sheath portion to a distal fluid supply end so that, when the first and second locking mechanism portions are mutually mated, the proximal dispensing portion of the fill needle is located inside the cavity and the distal fluid supply end of the fluid conduit is located outside the cavity. The fluid conduit may include a flexible tube in fluid communication with the proximal dispensing portion of the fill needle. The assembly may be a swab assembly with the implement portion comprising a swab disposed inside the cavity when the first and second locking mechanism portions are mutually mated.

The assembly may further comprise a controlled environment enclosure configured to aseptically isolate the process and hold the fluid handling assembly, and an articulated robot arm disposed within the enclosure to manipulate the fluid handling assembly. The first and second sheath portions may respectively comprise first and second engagement portions. The assembly may further comprise a robotic arm endpiece for the robotic arm, the endpiece configured to bear the first sheath portion by engagement with positive detent with the first engagement portion and a holding station comprising a first holding fixture to hold the second sheath portion, the fixture configured for engaging with the second engagement portion. The holding station may comprise angled fingers disposed to engage with the second engagement portion of the second sheath portion to release the first sheath portion from the second sheath portion. The holding station may comprise a second holding fixture configured to suspend the mutually engaged first and second sheath portions.

The first and second sheath portions may be separate injection molded parts and wherein the locking mechanism portions include at least one integrally molded spring member. The assembly may further include a tamper indicator that is mechanically linked to one of the locking mechanism portions and includes a portion that is constructed to irreversibly tear in response to the mechanical separation of the first and second sealing surfaces.

The first and second locking mechanism portions may be configured to mutually mate when the first and second locking mechanism portions are moved towards each other along a locking axis. The first sheath portion may further include a first bearing surface positioned at least generally normal to the locking axis, and the second sheath portion may further include a second bearing surface positioned at least generally normal to the locking axis and facing the first bearing surface.

In a further aspect a method is provided for automatically carrying out a fluid handling process in controlled environment enclosure, the method comprising providing a first implement inside a first sealed sheath, the first sheath sealed by a detent-based sealing mechanism on the first sheath that keeps the first sheath aseptically sealed around the first implement; placing the first sheath in the controlled environment enclosure; decontaminating the controlled environment enclosure around the first sheath after the step of placing; actuating the sealing mechanism to open the first sheath, and carrying out at least one step in the fluid handing process with the implement in the controlled environment enclosure. The step of providing may include providing a fill needle and wherein the step of carrying out includes carrying out a fill operation. The step of decontaminating may take place before the step of carrying out a fill operation, further including a step of again actuating the sealing mechanism to seal the first sheath.

The method may further include an additional step of decontaminating the controlled environment chamber after the steps of carrying out a fill operation and again actuating the sealing mechanism. The method may yet further include providing a swab inside a second sealed sheath, providing a second detent-based sealing mechanism on the second sheath that keeps the second sheath sealed around the swab, placing the second sheath in the controlled environment enclosure, wherein the step of decontaminating decontaminates the outside of the second sheath, and swabbing the fill needle after the step of carrying out a fill operation.

The method may further include the steps of removing the first implement and the first sheath from the controlled environment enclosure, discarding the first implement and the first sheath, providing a second implement inside a second sealed sheath, providing a second detent-based sealing mechanism on the second sheath that keeps the second sheath sealed around the second implement, placing the second sheath in the controlled environment enclosure, decontaminating the controlled environment enclosure around the second sheath, and carrying out at least one step in another run of the fluid handing process with the implement in the aseptic environment.

The steps of actuating the first sealing mechanism and carrying out the filling operation may be performed at least in part by a robotic arm disposed within the controlled environment enclosure. The method may further include the step of providing a pre-sterilized tube aseptically sealed to the fill needle. The step of carrying out a fill operation may include transferring fluid to at least one of a culture of cells, a culture of tissue, an enzyme solution, a suspension of immobilized enzymes, a mix of active ingredients, and an excipient. The step of carrying out a fill operation may include transferring fluid to at least one of microwell plates and containers for pharmaceutical products.

In a further aspect, a method is provided for automatically carrying out a fluid handling process in controlled environment enclosure, comprising: providing a plurality of disposable implements each aseptically sealed inside one of a plurality of disposable sheaths, placing a first of the plurality of sealed sheaths that contains a first of the plurality of implements in the controlled environment enclosure, decontaminating the controlled environment enclosure around the first sheath after the step of placing the first sheath, opening the first sheath, carrying out at least one step in the fluid handing process with the first implement in the controlled environment enclosure, removing the first sheath and the first implement from the controlled environment enclosure, discarding the first implement and the first sheath, placing a second of the plurality of sealed sheaths that contains a second of the plurality of implements in the controlled environment enclosure, decontaminating the controlled environment enclosure around the second sheath after the step of placing the second sheath, opening the second sheath, carrying out at least one step in another run of the fluid handing process with the second implement in the controlled environment, and repeating the steps of placing, decontaminating, opening, removing, and discarding for successive further ones of the plurality of disposable implements and corresponding ones of the plurality of disposable sheaths. The step of providing may provide a plurality of disposable implements that each include an intact tamper indicator. The steps of placing the first, second, and further sheaths may each include placing the intact tamper indicator for the sheath being placed, and the steps of opening the first, second, and further sheaths may each include disrupting the tamper indicator for the sheath being opened.

In a further aspect, a fluid handling assembly is provided for automatically carrying out a fluid handling process in an aseptic environment, comprising: a first sheath portion including an implement portion disposed within the first sheath portion for use in the process, a first locking mechanism portion, a first sealing portion, and a first bearing surface positioned at least generally normal to a locking axis; a second sheath portion including: a second locking mechanism portion configured to mate with the first locking mechanism portion when the first and second locking mechanism portions are moved towards each other along the locking axis, a second sealing portion disposed to aseptically seal with the first sealing portion when the first and second locking mechanism portions are mutually mated, and a second bearing surface positioned at least generally normal to the locking axis and facing toward the first bearing surface, wherein the first and second sheath portions define a sealed cavity that aseptically encapsulates the implement portion when the first and second locking mechanism portions are mutually mated.

In a further aspect, a fluid handling assembly is provided for automatically carrying out a fluid handling process in an aseptic environment, comprising: a first sheath portion including a swab disposed within the first sheath portion for use in the process, and a first sealing portion; and a second sheath portion including a second sealing portion disposed to aseptically seal with the first sealing portion, wherein the first and second sheath portions define a sealed cavity that aseptically encapsulates the swab when the first and second sealing portions are mutually mated.

In a further aspect, a method is provided for automatically carrying out a fluid handling process in controlled environment enclosure, comprising: providing a swab inside a first aseptically sealed sheath, placing the first sheath in the controlled environment enclosure, decontaminating the controlled environment enclosure around the first sheath after the step of placing, opening the first sheath, and swabbing an implement used in the fluid handing process with the swab in the controlled environment enclosure.

In another aspect, a method is provided for aseptically filling a pharmaceutical container with a pharmaceutical fluid, the method comprising: in a chamber capable of maintaining an aseptic condition providing a fill needle comprising a fill needle tubing having a dispensing tip; establishing in the chamber an aseptic condition; providing in the chamber at least one aseptic pharmaceutical container comprising a container opening; moving at least one of the fill needle and the at least one container to dispose the fill needle over the container opening; dispensing the pharmaceutical fluid through the dispensing tip and the container opening into the at least one container; halting the dispensing to retain within the fill needle a terminal pharmaceutical fluid portion; and automatically removing the terminal pharmaceutical fluid portion from the fill needle into the container after halting the dispensing. The method may further comprise providing a controller. The removing may be automatically initiated and terminated by the controller.

Automatically removing the terminal pharmaceutical fluid portion may comprise injecting an aseptic gas into the fill needle tubing. Providing the fill needle may comprise providing a fill needle having a gas inlet orifice in the fill needle tubing proximate the dispensing tip; and injecting the aseptic gas into the fill needle tubing may comprise injecting the aseptic gas via the orifice. Injecting an aseptic gas into the fill needle tubing may comprise injecting at least one of aseptic nitrogen gas, aseptic air and aseptic helium gas. Injecting an aseptic gas into the fill needle tubing may comprise filtering the gas to render it aseptic. The method may comprise maintaining a flow of the gas until no more pharmaceutical fluid is removed from the fill needle. In another embodiment, automatically removing the terminal pharmaceutical fluid portion may comprise inflating a bladder within the dispensing tip.

Providing the fill needle may comprise providing a flexible terminal tube disposed within the dispensing tip and a compression actuator disposed to compress the flexible terminal tube; and automatically removing the terminal pharmaceutical fluid portion may comprise automatically operating the compression actuator to compress the flexible terminal tube. Operating the actuator may comprise piezoelectrically actuating the actuator or electromechanically actuating the actuator.

Providing the fill needle may comprise providing the fill needle tubing with a vibration actuator disposed on the fill needle tubing for shaking the dispensing tip; and automatically removing the terminal pharmaceutical fluid portion may comprise automatically operating the vibration actuator to shake the dispensing tip. Providing the fill needle may comprise providing a fill needle having a gas channel surrounding the fill needle tubing, the gas channel having an annular opening with respect to and proximate to the dispensing tip; and wherein automatically removing the terminal pharmaceutical fluid portion may comprise blowing an aseptic gas at the terminal pharmaceutical fluid portion. Providing the fill needle may comprise providing a fill needle having a gas channel, the gas channel having an annular opening with respect to and proximate the dispensing tip; and wherein automatically removing the terminal pharmaceutical fluid portion may comprise blowing an aseptic gas at the terminal pharmaceutical fluid portion through the annular opening.

Providing a fill needle may comprise providing a first robotic arm having a first end effector; and moving the fill needle may comprise engaging the fill needle with the first end effector and operating the robotic arm. Providing a first robotic arm may comprise providing a first articulated robotic arm. Providing the at least one container may comprise providing a container nest bearing the at least one container. Providing the container nest may further comprise providing a second robotic arm having a second end effector; and moving the at least one container may comprise engaging the container nest with the second end effector and operating the second robotic arm. Providing the second robotic arm may comprise providing a second articulated robotic arm. In another embodiment, providing the container nest may comprise providing the container nest held in a locating structure of a rotary stage, and moving the at least one container may comprise rotating the rotary stage.

Providing the fill needle may comprise providing the fill needle closed with a fill needle sheath; sterilizing the chamber to establish within the chamber an aseptic condition; and disengaging and removing the fill needle from the fill needle sheath. The method may further comprise engaging the fill needle with the fill needle sheath after removing the terminal pharmaceutical fluid portion from the fill needle.

In a further aspect, a fill needle system is presented for aseptically dispensing a pharmaceutical fluid in a chamber capable of maintaining an aseptic condition, the system comprising: a fill needle hub, a fill needle tubing in fluid communication with a pharmaceutical fluid source and extending through the fill needle hub; a fill needle dispensing tip disposed at a dispensing end of the fill needle tubing; a fill needle sheath shaped and arranged to removably mate with and seal aseptically to the fill needle hub to form an aseptically sealed volume enclosing the dispensing tip; and a terminal fluid ejector disposed and configured for removing a terminal pharmaceutical fluid portion from the dispensing tip.

The terminal fluid ejector may comprise a gas channel in fluid communication with the dispensing tip via an orifice located in the fill needle tubing fluidwise immediately upstream from the dispensing tip. The system may further comprise a gas source for supplying aseptic gas to the gas channel. The system may further comprise a gas filter disposed to filter the gas from the gas source in order to supply aseptic gas to the gas channel.

In another embodiment, the terminal fluid ejector may comprise a bladder disposed and arranged to remove the terminal pharmaceutical fluid portion from the dispensing tip when expanded under the action of gas pressure. In another embodiment the terminal fluid ejector may comprise a flexible terminal tube and an electromechanical actuator or piezoelectric actuator that is disposed and arranged to compress the flexible terminal tube.

In further embodiments, the terminal fluid ejector may comprise a gas channel surrounding the fill needle tubing, the gas channel having an annular opening with respect to and proximate to the dispensing tip disposed to direct gas via the gas channel toward the dispensing tip. In yet further embodiments, terminal fluid ejector may comprise a vibration actuator disposed on the fill needle tubing and arranged for shaking the dispensing tip.

The system may further comprise a controller configured to control the dispensing of the pharmaceutical fluid via the dispensing tip. The controller may be configured to automatically operate the terminal fluid ejector to remove the terminal pharmaceutical fluid portion after halting the dispensing of the pharmaceutical fluid.

In a further aspect, a method is provided for aseptically filling a pharmaceutical container with a pharmaceutical fluid, the method comprising: in a chamber capable of maintaining an aseptic condition providing a fill needle system comprising a fill needle, the fill needle comprising fill needle tubing in fluid communication with a dispensing tip; establishing in the chamber an aseptic condition; providing in the chamber at least one aseptic pharmaceutical container comprising a container opening; moving at least one of the fill needle and the at least one container to dispose the fill needle over the container opening; dispensing the pharmaceutical fluid via flexible tubing through the dispensing tip and the container opening into the at least one container; halting the dispensing to retain on the dispensing tip a pharmaceutical fluid droplet; and inducing a pressure pulse in the fluid in the fill needle tubing to dislodge the droplet from the dispensing tip into the container.

Providing the fill needle system may comprise providing a fluid pressure pulse induction system and flexible tubing in fluid communication with the fill needle tubing and the dispensing tip, and the fluid pressure pulse induction system may be disposed and configured to compress the flexible tubing. Inducing the pressure pulse in the fluid may comprise operating the fluid pressure pulse induction system to compress the flexible tubing. Compressing the flexible tubing may comprise annularly compressing the flexible tubing.

The method may further comprise providing a controller operably coupled to the fluid pressure pulse induction system for controlling the inducing of a pressure pulse in the fluid in the fill needle tubing. The dispensing and the inducing a pressure pulse in the fluid in the fill needle tubing may be automatically controlled by the controller.

The method may further comprise moving at least one of the fill needle and the at least one container to dispose the fill needle over the container opening. The method may further comprise providing in the chamber a first robotic arm having a first end effector, and moving the fill needle may comprise engaging the fill needle with the first end effector and operating the robotic arm. Providing a first robotic arm may comprise providing a first articulated robotic arm. The providing the at least one container may comprise providing the at least one container in a container nest. The method may further comprise providing a second robotic arm having a second end effector, wherein moving the at least one container comprises engaging the container nest with the second end effector and operating the second robotic arm. Providing a second robotic arm may comprise providing a second articulated robotic arm.

Providing the at least one container may comprise providing the at least one container in a container nest held in a locating structure of a rotary stage, and moving the at least one container may comprise rotating the rotary stage.

Providing the fill needle may comprise: providing the fill needle closed with a fill needle sheath; sterilizing the chamber to establish within the chamber an aseptic condition; and disengaging and removing the fill needle from the fill needle sheath. The method may further comprise engaging the fill needle with the fill needle sheath after dislodging the droplet from the dispensing tip.

In a further aspect, a fill needle system for aseptically dispensing a pharmaceutical fluid in an aseptic chamber comprises a fill needle tubing in fluid communication with a pharmaceutical fluid source via flexible tubing and extending through a fill needle hub; a fill needle dispensing tip disposed at a dispensing end of the fill needle tubing; a fill needle sheath shaped and arranged to removably mate with and seal aseptically to the fill needle hub to form an aseptically sealed volume enclosing the dispensing tip; and a fluid pressure pulse induction system disposed and configured to compress the flexible tubing in order to dislodge droplets of pharmaceutical fluid retained on the dispensing tip after halting dispensing of the fluid.

The system may comprise a controller configured to control the dispensing of the pharmaceutical fluid via the dispensing tip. The controller may be configured to operate the fluid pressure pulse induction system to automatically compress the flexible tubing after halting dispensing of the pharmaceutical fluid. The controller may be configured to induce in the fill needle tubing a pressure pulse of predetermined fluid amplitude and duration selected to specifically dislodge only a single droplet of pharmaceutical fluid retained on the dispensing tip after halting dispensing of the pharmaceutical fluid.

The fluid pressure pulse induction system may be disposed and configured to annularly compress the flexible tubing. The fluid pressure pulse induction system may be piezoelectrically, pneumatically, electromechanically, or magnetically actuated.

Other features, elements, steps, characteristics and advantages of the present invention will become more apparent from the following detailed description of preferred embodiments of the present invention.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9A and FIG. 9B show isometric and sectional views respectively of a combination of a fill needle and a fill needle sheath, while

DETAILED DESCRIPTION

Figure 1:
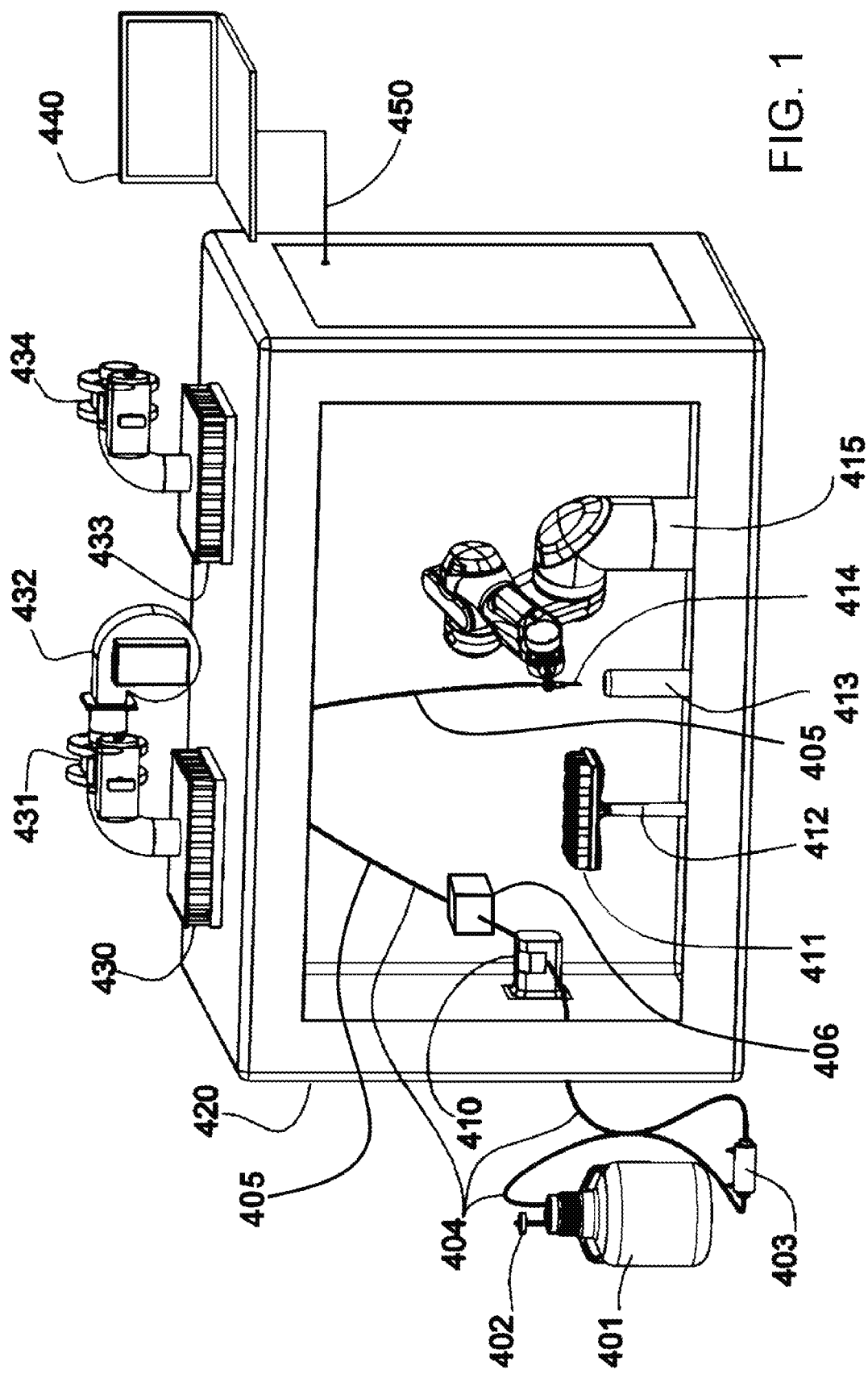
FIG. 1 shows an apparatus for the protecting and unprotecting of a fluid path in a controlled environment enclosure.

FIG. 1 shows an embodiment of an apparatus for protecting and unprotecting of fluid path 404 in controlled environment enclosure 420. The term "fluid" as used herein denotes any liquid, gas, liquid-gas mixtures and any mixture of solids in liquid that has fluid attributes, such as flowability or having appreciable fluidity at ambient temperature and pressure, including, without limitation, a dispersion of a solid or solids in a liquid, an emulsion, a slurry, a microemulsion, colloidal suspension, a suspension, a suspension of liposomes, and a suspension of micelles or the like. The term "fluid path" as used herein denotes any single channel or multi channel tubing or other pathway or structure, rigid or flexible, for transporting a fluid.

Fluid path 404 starts at container 401. The term "container" as used herein denotes any vessel suitable to hold a fluid, including without limitation any vial, syringe, ampoule, carpule, bottle, flask, beaker, bag, well in multiwell plates, tub or tube. Container 401 is fitted with air filter 402. Container 401 may be equipped with optional sensors (not shown) to measure volume, weight of fluid, or other parameters. In some embodiments there may be multiple containers connected in parallel or in series with one another. Along fluid path 404 there may be optional measuring devices (not shown) that measure properties, including without limitation any one or more of pressure, flow, temperature, density and conductivity. Fluid path 404 may be fitted with filter element 403. Filter element 403 may be selected to be suitable for sterile filtration of fluids.

In FIG. 1 fluid path 404 comprises flexible tubing 405 and enters controlled environment enclosure 420 via a sealed opening (not shown). The sealing may be, for example, via the use of a suitable aseptically sealing flange (not shown), which may seal by means of, for example without limitation, an aseptic tri-clamp. Container 401 and air filter 402 may be located outside controlled environment enclosure 420, as shown in FIG. 1. In other embodiments of the invention container 401 and air filter 402 may be located inside controlled environment enclosure 420. Fluid pulse induction subsystem 406 may or may not be present within fluid path 404, and will be described in detail later below at the hand of FIG. 24.

Controlled environment enclosure 420 is equipped with inlet filter 430, inlet valve 431, blower 432, outlet filter 433 and outlet valve 434. The characteristics of blower 432, inlet filter 430 and outlet filter 433 are chosen to yield a controlled environment inside controlled environment enclosure 420. As understood by those skilled in the art, various other filter and blower arrangements are possible to establish a controlled environment inside controlled environment enclosure 420. A suitable controlled environment may be obtained, for example without limitation, by means of any one or more of turbulent airflow, horizontal unidirectional airflow and vertical unidirectional airflow.

The fluid from container 401 may be transferred through fluid path 404 by a variety of one or more different mechanisms, including without limitation peristaltic pump 410 as shown in FIG. 1, a difference in pressure between container 401 and controlled environment enclosure 420, a difference in static height of container 401 and the end of fluid path 404, a gear pump, a lobe pump, a membrane pump, a piston pump, or a syringe pump. In FIG. 1, pump 410 is shown disposed inside controlled environment enclosure 420. In other embodiments, pump 410 may be disposed outside controlled environment enclosure 420.

Flexible tubing 405 of fluid path 404 may terminate with end piece 414. A suitable end piece may be, for example without limitation, a fill needle, a pipette dispensing system, a syringe dispensing system, a valve dispensing system, quick connectors, aseptic connectors, dispense tips and a needle for piercing of elastomers. In FIG. 1 end piece 414 is selected to include a fill needle.

End piece 414 may be manipulated inside controlled environment enclosure 420 by mechanical means, for example, robotic arm manipulation system 415. One suitable robotic arm manipulation system 415 may be an articulated robotic arm. Suitable robotic arm manipulation systems for mechanically manipulating end piece 414 include, but are not limited to, 6-axis robotic arms, Selective Compliant Articulated Robot Arm (SCARA) systems, r-theta robots, or combinations of linear actuators and rotary actuators.

Fluids are transferred along fluid path 404 to a destination, which may be containers such as the tray with vials 411 located on pedestal 412 in FIG. 1. The destination may be microwell plates for pharmaceutical products.

Fluid path 404 may be employed for a variety of purposes including without limitation the filling of empty containers, washing and rinsing of containers, adding fluid to containers with a freeze dried powder, adding fluids to containers containing excipients and/or active ingredients, adding medium to cells, tissue or microbes, inoculating cells or microbes, adding substrate to enzyme solutions or suspensions of immobilized enzymes, adding gases such as argon or nitrogen to create an inert head space in containers, adding gases such as nitrogen, air or carbon dioxide to cells and removing fluids out of containers by suction. The term "excipient" as used herein denotes an inert substance used as a diluent or vehicle for a drug.

Fluid path 404 may in some applications be required for aseptic transfer of fluids. In such a case fluid path 404 may be pre-sterilized before installation in controlled environment enclosure 420. The aseptic part of fluid path 404 may start with container 401 or with filter 403. Installation of aseptic fluid path 404 requires sealing of end piece 414.

Figure 4:
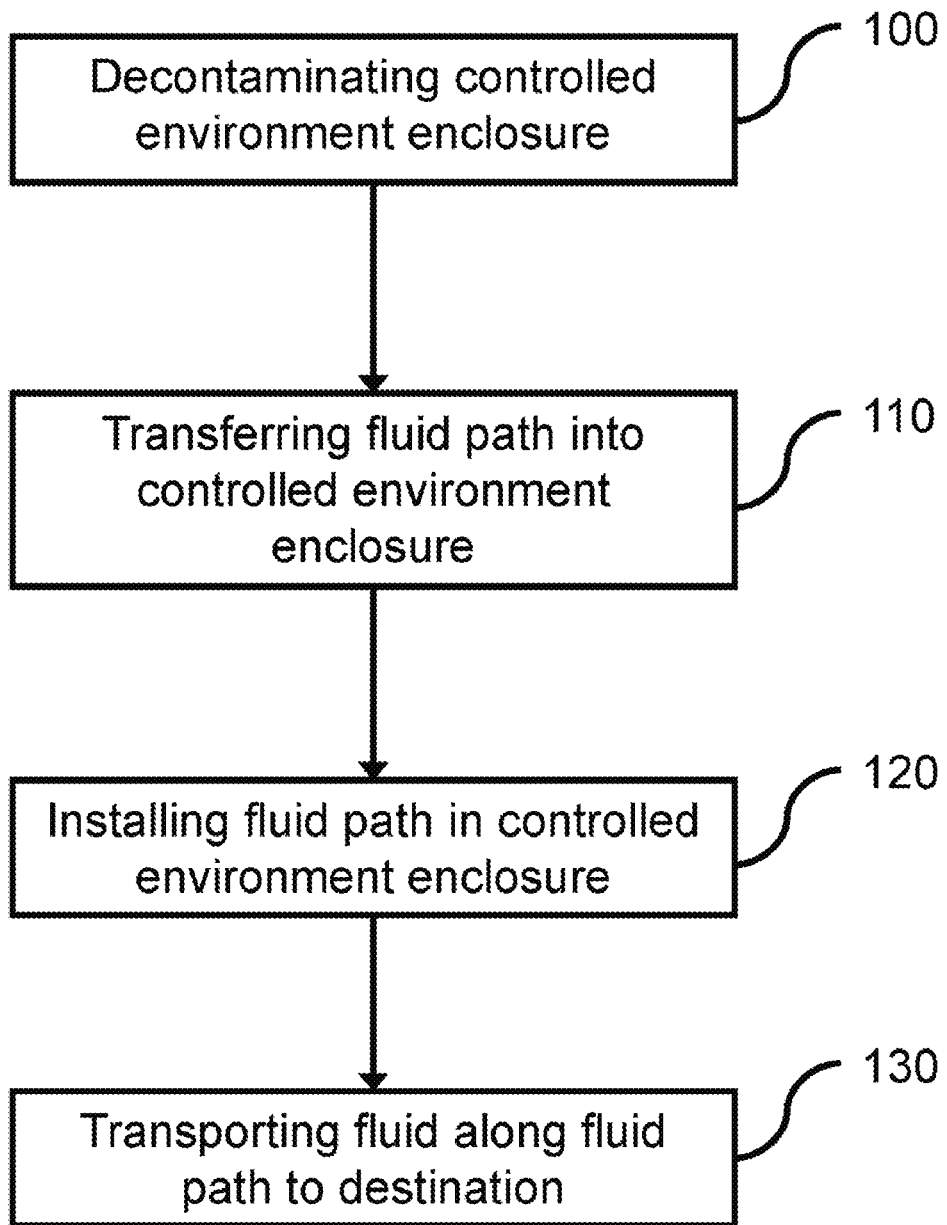
FIG. 4 is a flow chart for the typical prior art method.

FIG. 4 is a flowchart showing the prior art method for installing a fluid path in a prior art controlled environment enclosure. The prior art method requires the steps in sequence of decontaminating [100] the prior art controlled environment enclosure; transferring [110] the fluid path into the prior art controlled environment enclosure; and installing [120] by hand the fluid path in the prior art controlled environment enclosure, before using [130] the fluid path for the purpose for which it is intended.

Figure 5:
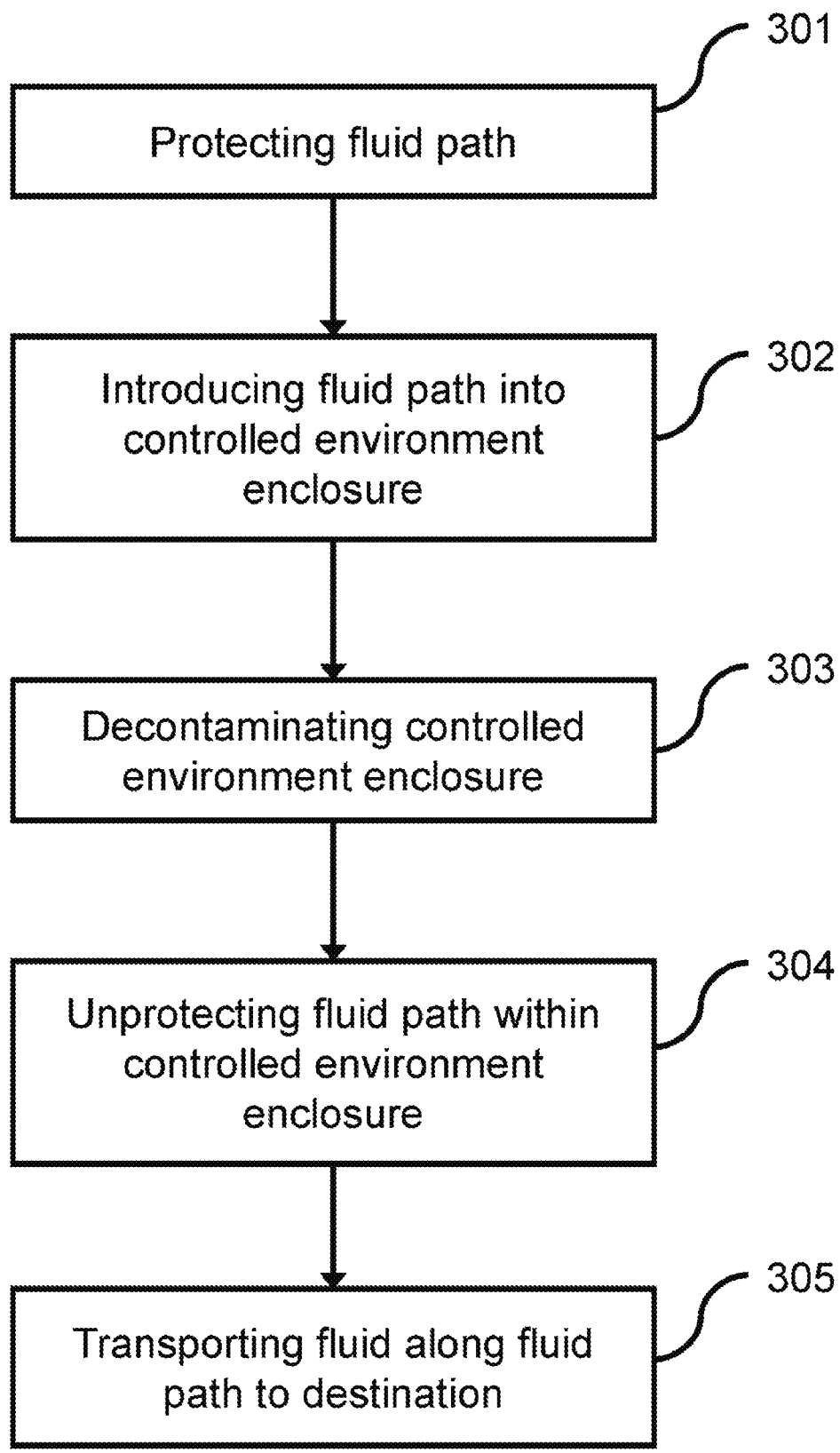
FIG. 5 shows a method flow chart of an aspect of the invention.

In an aspect of the invention there is provided a method for installing fluid path 404 in controlled environment enclosure 420. Referring to the apparatus of FIG. 1 and the flow chart of FIG. 5, the method comprises protecting [301] fluid path 404 against an environment external to fluid path 404, introducing [302] fluid path 404 into controlled environment enclosure 420, decontaminating [303] controlled environment enclosure 420, and mechanically unprotecting [304] fluid path 404. In its unprotected state fluid path 404 may then be used for transporting [305] fluids to destination 411, which fluids may be aseptic or sterile fluids. Such transporting [305] of fluids may comprise filtering the fluid in fluid path 404 using filter element 403 and the filtering may be sterile filtering. The terms "sterile" and "aseptic" are used interchangeably in this specification. The term "decontamination" as used herein denotes a process for removing or inactivating contamination, including without limitation viruses, bacteria, spores, prions, molds, yeasts, proteins, pyrogens and endotoxins, to acceptable levels. "Decontamination" as used herein includes both sterilization (that is, the destruction of all microorganisms, including bacterial spores to a probability of surviving organisms of typically less than $1:10^6$) and disinfection (that is, the destruction and removal of specific types of micro-organisms).

Figure 2:
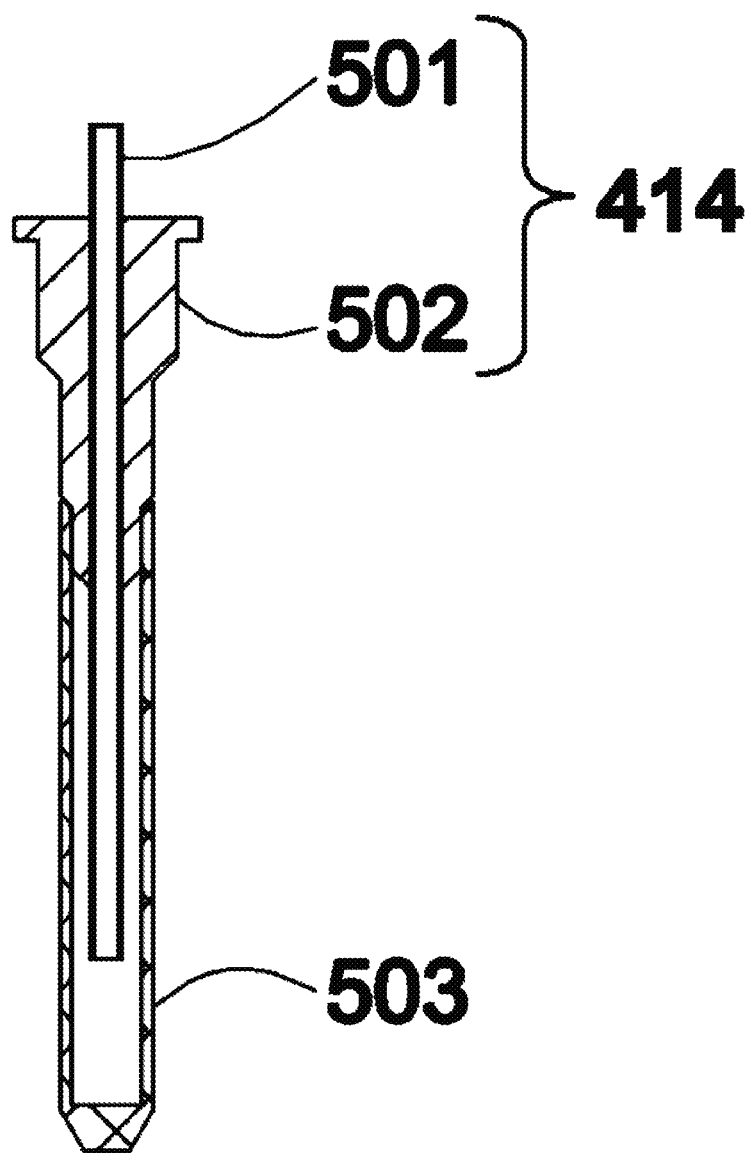
FIG. 2 shows detail of an end piece of an apparatus for the protecting and unprotecting of a fluid path in a controlled environment enclosure

In FIG. 2 a suitable arrangement for mechanically unprotecting [304] fluid path 404 is shown, comprising end piece 414 of fluid path 404 in the form of a fill needle, together with fill needle sheath 503. Fill needle 414 comprises fill needle tubing 501 and fill needle hub 502. Fill needle tubing 501 is in fluid communication with fluid path 404 of FIG. 1 and is aseptically joined to fluid path 404. When fluid path 404 is within controlled environment enclosure 420, fill needle sheath 503 may be stored in sheath removal station 413 of controlled environment enclosure 420 shown in FIG. 1.

Fill needle hub 502 and fill needle tubing 501 may be glued or welded together. In alternative embodiments fill needle hub 502 and fill needle tubing 501 may be made as one part out of solid material. Fill needle sheath 503 may be manufactured using materials with different thermal expansion coefficients to allow it to slide on and off fill needle hub 502 after thermal expansion. Alternatively, fill needle sheath 503 may be designed to have a sliding fit on fill needle hub 502 using porous PTFE or a steam permeable elastomeric material.

Protecting [301] fluid path 404 comprises sealingly placing fill needle sheath 503 over fill needle 414 such that fill needle sheath 503 seals with needle hub 502. Fill needle sheath 503 and needle hub 502 may be equipped with one or multiple of tamper evident features 504 that will provide evidence of breaking the seal between needle hub 502 and fill needle sheath 503. Possible tamper evident features 504 include but are not limited to heat shrink bands, tape seals, breakable rings, tear-off connectors and snap connect tear-off connectors. Unprotecting [304] fluid path 404 comprises removing fill needle sheath 503 from fill needle 414, thereby exposing fill needle 414 to an environment within controlled environment enclosure 420. When fill needle 414 is in use within controlled environment enclosure 420, fill needle sheath 503 is stored in sheath removal station 413.

Figure 3:
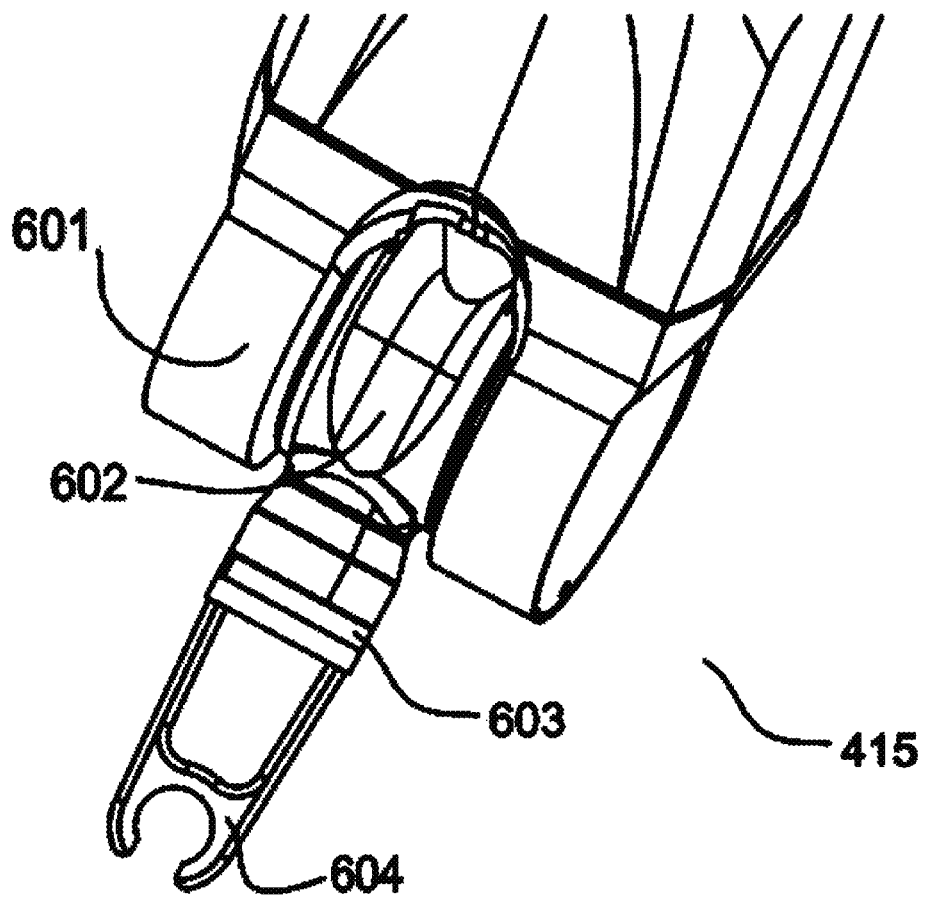
FIG. 3 shows detail of a robotic arm forming part of an apparatus for the protecting and unprotecting of a fluid path in a controlled environment enclosure

Mechanically unprotecting [304] fill needle 414 when it is within controlled environment enclosure 420 may comprise using robotic arm manipulation system 415 shown in FIG. 1. FIG. 3 illustrates part of robotic arm manipulation system 415 of FIG. 1, wherein forearm 601 is connected to wrist 602, and wrist 602 is connected to tool flange 603. End tool 604, shown in FIG. 3 as being fork shaped, has a partially opened bore of such diameter that end tool 604 may slide around a narrow tubular section of needle hub 502 and end tool 604 may move upwards to establish a precise locating fit to needle hub 502. For unprotecting [304] fill needle 414, end tool 604 moves fill needle 414 with fill needle sheath 503 and places fill needle 414 with fill needle sheath 503 in sheath removal station 413.

In one embodiment of the apparatus and method, sheath removal station 413 heats fill needle sheath 503, which thereby expands and releases its grip or seal to needle hub 502. Practitioners in the field will appreciate that there are many different procedures and methods by which fill needle sheath 503 may be removed from fill needle 414. End tool 604, through the motion of robotic arm manipulation system 415, removes fill needle 414 from fill needle sheath 503. Fill needle sheath 503 may remain in sheath removal station 413 while robotic arm manipulation system 415 moves fill needle 414 to the destination. In one embodiment of the apparatus and method the destination shown is the tray with vials 411 located on pedestal 412 in FIG. 1.

End tool 604 and needle hub 502 may have various different other shapes allowing the use of various other closure systems such as, for example without limitation, a plug, a cap with sliding fit o-ring seal with minimal occluded surface area, a cap with membrane peel-off seal, or a twist-off cap. As understood by those skilled in the art, some closure systems are more suitable than other closure systems for use with particular sterilization methods.

Materials of lesser permeability may be used in the manufacture of flexible tubing 405, but this is not always an option. Tubing permeability may also be reduced by adding additional layers to the tubing. Example methods for establishing such additional layers around flexible tubing 405 include, but are not limited to, heat shrinking with non-permeable polymers such as PEP, multilayer co-extrusion with non-permeable polymers, creating a diffusion barrier by polymeric coating such as poly(p-xylylene), encasing with layers of tape, and the fitting of a sleeve.

Figure 6:
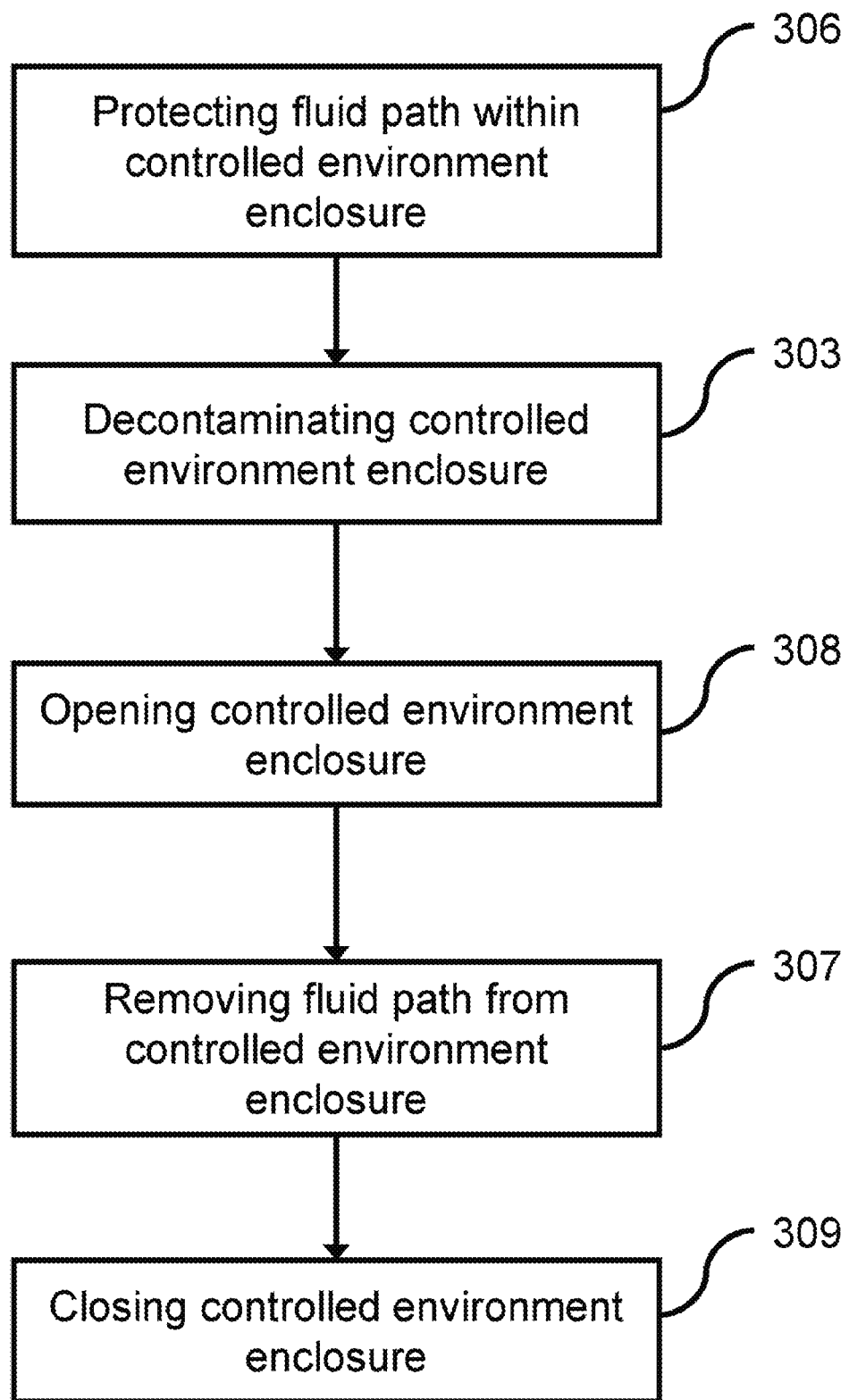
FIG. 6 shows a method flow chart of another aspect of the invention.

In a further aspect of the invention there is provided a method for uninstalling fluid path 404 from controlled environment enclosure 420. Referring to the apparatus of FIG. 1 and the flow chart of FIG. 6, the method comprises mechanically protecting [306] fluid path 404 within controlled environment enclosure 420 once the use of fluid path 404 has been completed, decontaminating [303] controlled environment enclosure 420, and removing [307] fluid path 404 from controlled environment enclosure 420. Mechanically protecting [306] fill needle 414 may comprise using robotic arm manipulation system 415 shown in FIG. 1.

Mechanically protecting [306] fill needle 414 within controlled environment enclosure 420 may comprise using robotic arm manipulation system 415 of FIG. 1. End tool 604 (See FIG. 3) of robotic arm manipulation system 415 is used to move fill needle 414 to and place it in fill needle sheath 503, which is housed in sheath removal station 413. Sheath removal station 413 heats fill needle sheath 503 until fill needle sheath 503 may slide over fill needle 414 to suitably seal to needle hub 502 after cooling, to thereby protect [306] fill needle 414 within controlled environment enclosure 420. Robotic arm manipulation system 415 may then further move protected fluid path 404 as may be required.

In a further aspect of the invention, mechanically unprotecting [304] and mechanically protecting [306] fill needle 414 using robotic arm manipulation system 415 may be done automatically. For example, suitable controller 440 (see FIG. 1), communicating control instructions with controlled environment enclosure 420 via control line 450, may be programmed to automatically unprotect [304] fill needle 414 using robotic arm manipulation system 415 once decontaminating [303] controlled environment enclosure 420 has been completed. Such automation obviates human intervention in the step of mechanically unprotecting [304] fill needle 414. In an embodiment of the method, the step of decontaminating [303] controlled environment enclosure 420 may also be managed by controller 440. This allows the remainder of the steps of installing fill needle 414, beyond the step of introducing [302] fluid path 404 into controlled environment enclosure 420, to be automated using controller 440, including the use of the fill needle for the purpose for which it is installed, and mechanically protecting [306] fill needle 414 after such use.

Figure 7:
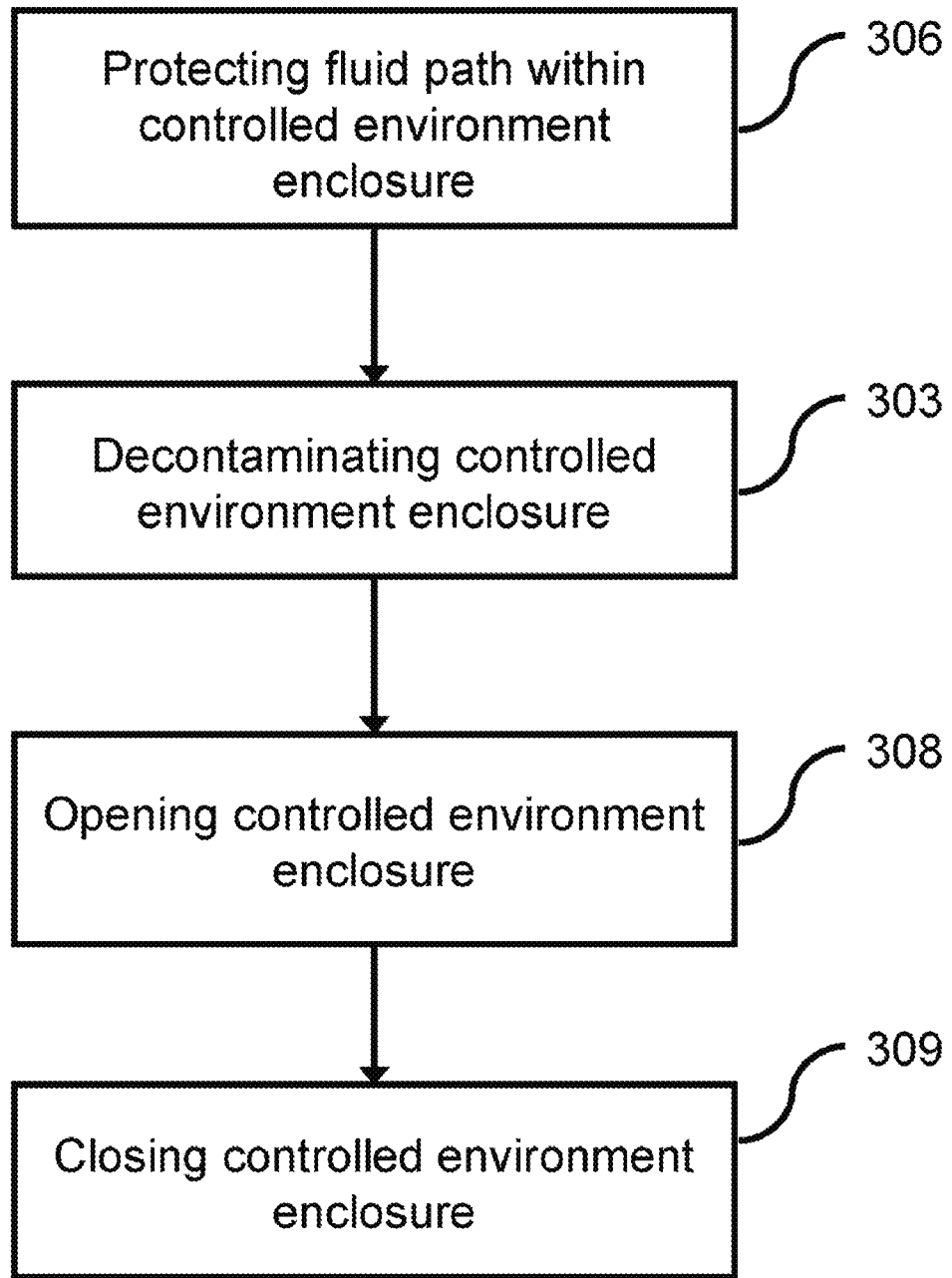
FIG. 7 shows a method flow chart of another aspect of the invention.
Figure 8:
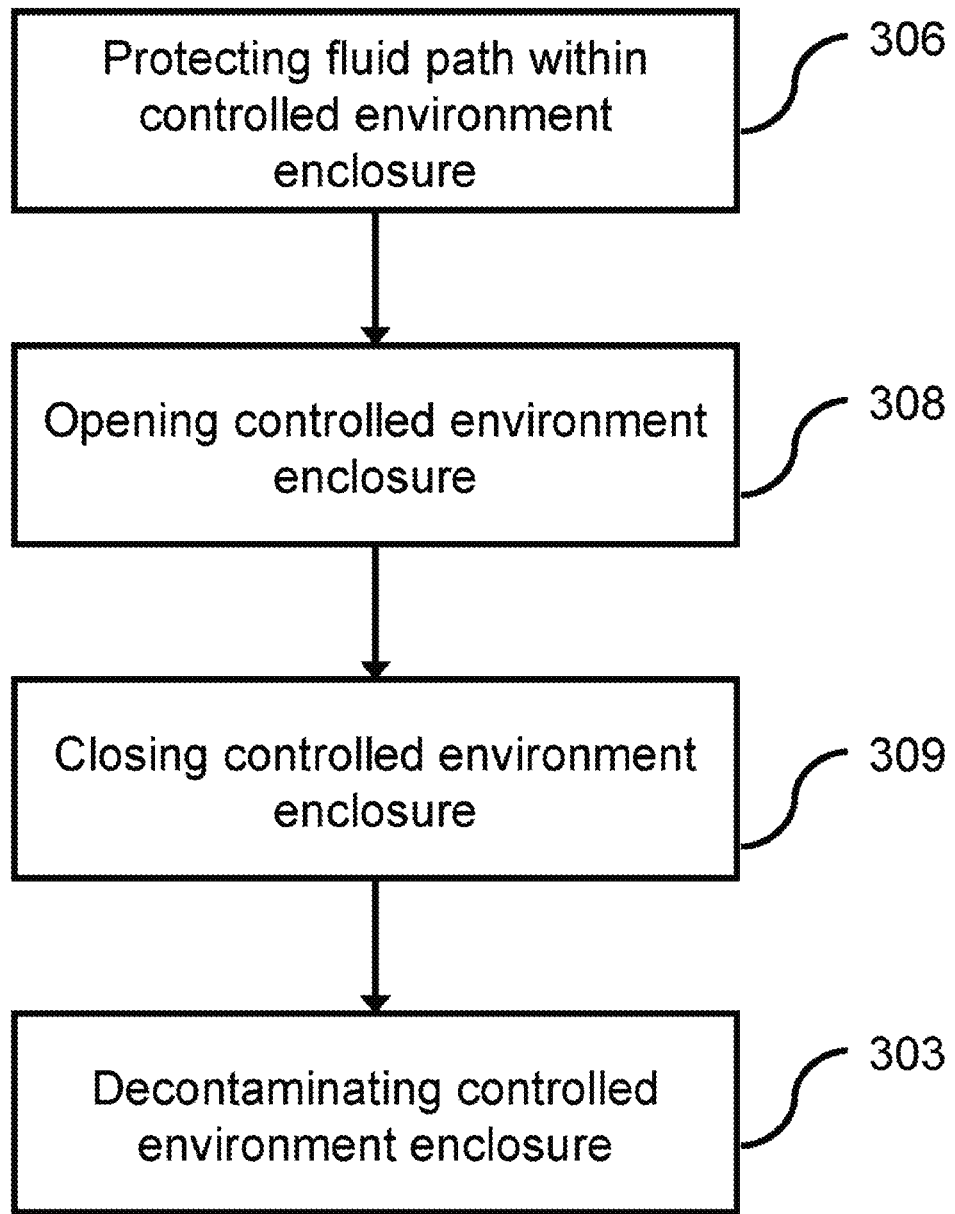
FIG. 8 shows a method flow chart of another aspect of the invention.

In a further aspect of the invention there is provided a method for decontaminating controlled environment enclosure 420 having fluid path 404. The method comprises mechanically protecting [306] fluid path 404 within the controlled environment enclosure by sealingly placing fill needle sheath 503 over fill needle 414 such that fill needle sheath 503 seals with needle hub 502; decontaminating [303] controlled environment enclosure 420; and opening [308] and closing [309] controlled environment enclosure 420. Opening [308] and closing [309] controlled environment enclosure 420 may be done after decontaminating [303] controlled environment enclosure 420, as may be the case when the fluid or the materials at the destination 411 are dangerous. This is shown in FIG. 7. Alternatively, opening [308] and closing [309] controlled environment enclosure 420 may be done before decontaminating [303] controlled environment enclosure 420. This is shown in FIG. 8, as may be the case when the external environment holds potential of contaminating the fluid or the materials at the destination 411. Mechanically protecting [306] fill needle 414 may comprise using robotic arm manipulation system 415 shown in FIG. 1, as already described.

Protecting [306] fill needle 414 using robotic arm manipulation system 415 may be done automatically via controller 440 (see FIG. 1). Controller 440 may be programmed for automatically mechanically protecting [306] fill needle 414 using robotic arm manipulation system 415, prior to opening [308] and closing [309] the controlled environment enclosure 420. Opening [308] and closing [309] controlled environment enclosure 420 may likewise be automated via controller 440.

We have described thus far herein an embodiment of sheath removal station 413 of FIG. 1 based on employing heat to secure or release fill needle 414 from fill needle sheath 503. We now turn to another embodiment of the subsystem comprising sheath removal station 413', fill needle 414', fill needle sheath 503', and robotic arm manipulation system 415 described at the hand of FIGS. 9A, 9B, 10 and 11. In this embodiment, we describe an alternative sheath removal system and associated sheath removal station 413', and provide more detail as regards fill needle 414', fill needle sheath 503', and robotic arm manipulation system 415.

Figure 9A:
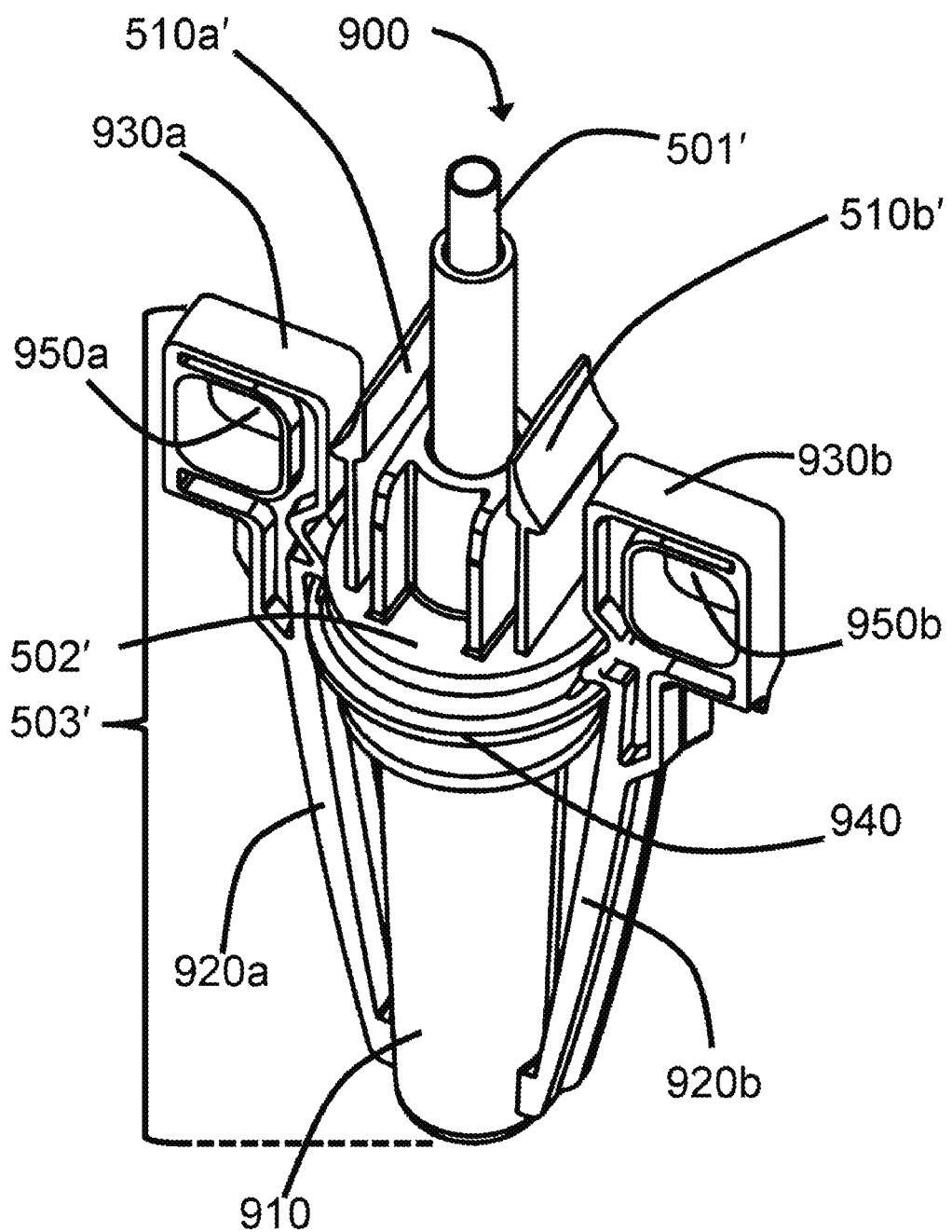
Figure 9B:
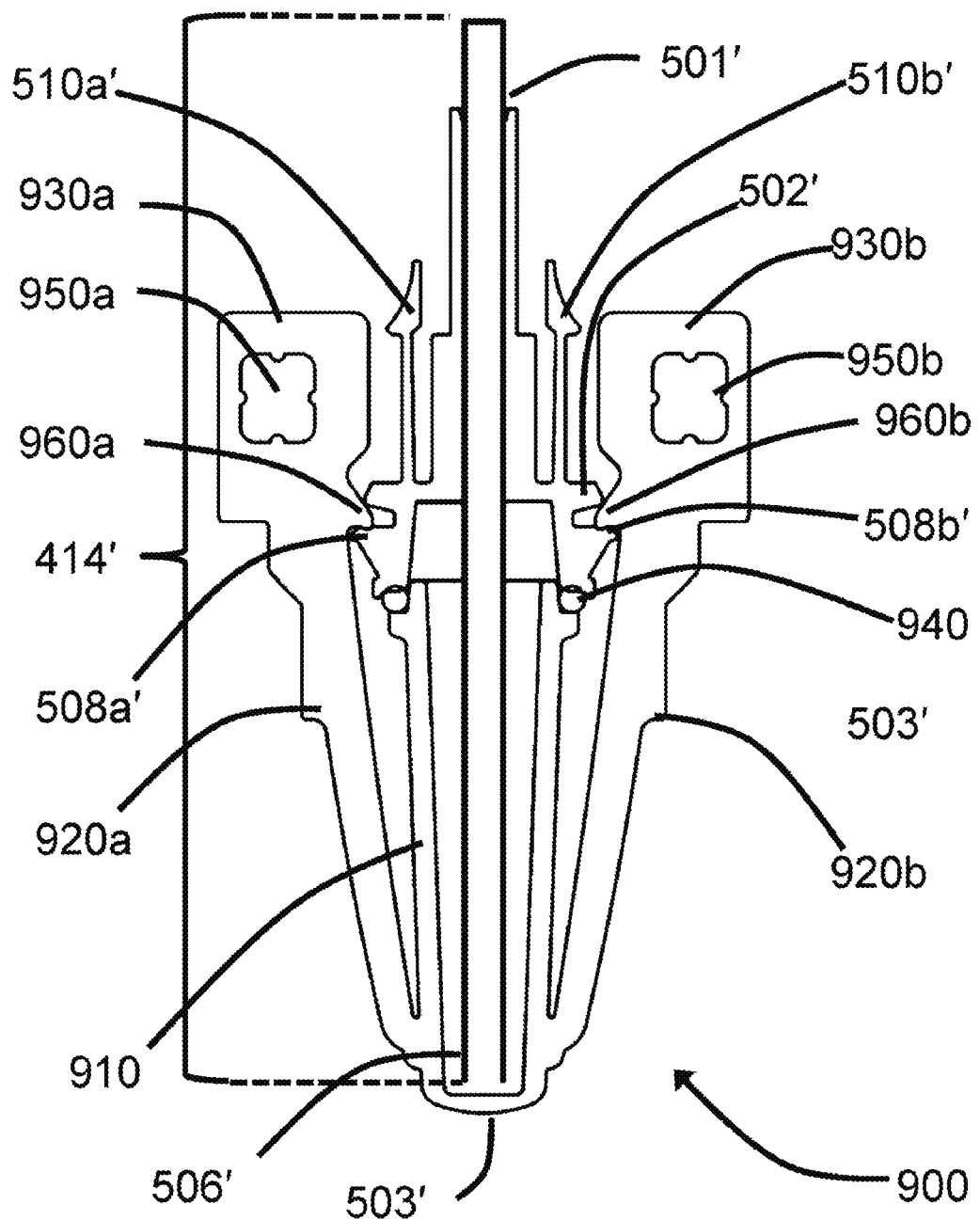

FIG. 9A and FIG. 9B provide isometric and sectional views respectively of fill needle sheath 503' and fill needle 414' combination 900 of this embodiment. The term "aseptically sealed fill needle package" 900 will be used in the present specification to describe this combination of mutually aseptically sealed fill needle sheath 503' and fill needle 414'. While FIG. 9A provides perspective, the simplicity of FIG. 9B allows more elements to be clearly indicated and numbered. Fill needle sheath 503' comprises a substantially cylindrical vessel portion 910 configured to receive the dispensing end of fill needle 414', and two clamping members 930a and 930b attached to vessel portion 910 by spring loaded members 920a and 920b respectively. In one embodiment, shown in FIG. 9A and FIG. 9B, the spring loading is established by means of the natural elastic flexibility of members 920a and 920b. To this end, fill needle sheath 503' may be manufactured from a polymeric material with suitable inherent elasticity and that is compatible with aseptic systems requirements. Locating eyelets 950a and 950b are disposed in clamping members 930a and 930b respectively. Clamping members 930a and 930b further comprise clamping clips 960a and 960b respectively disposed to engage with filling needle 414' as described in more detail below.

Filling needle 414' may be configured in many different ways. In the present non-limiting exemplary embodiment, fill needle 414' comprises fill needle tubing 501' and fill needle hub 502'. Fill needle 414' comprises dispensing portion 506', being the dispensing tip of fill needle 414'. Fill needle tubing 501' is in fluid communication with fluid path 404 of FIG. 1 and is aseptically joined to fluid path 404. Fill needle hub 502' mates axially face-to-face with fill needle sheath 503' in an aseptic pressure seal provided by elastically compressible O-ring 940. Fill needle hub 502' further comprises locating ledges 508a' and 508b' for engaging with clamping clips 960a and 960b of filling needle 414'. In manufacture, spring loaded members 920a and 920b are fashioned to be spring loaded when clamping clips 960a and 960b are engaged with locating ledge 508'. When filling needle 414' is sheathed in fill needle sheath 503' with compressible O-ring 940 under suitable compression, clamping clips 960a and 960b are engaged with locating ledge 508' and under a tension force directing clips 960a and 960b towards each other. Under these circumstances, the tension in fill needle sheath 503' is contained in spring loaded members 920a and 920b. Other embodiments for urging clips 960a and 960b towards each other when filling needle 414' is sheathed in fill needle sheath 503' are contemplated, including embodiments in which discrete springs are employed to render members 920a and 920b spring loaded.

Fill needle sheath 503' may be manufactured by injection molding of a suitable polymeric material. In order to keep units costs low it may specifically be injection molded as a single monolithic unit. In the present specification the term "monolithic" is employed to describe an object that is fashioned is a contiguous whole from one piece of material without joints or seams, whether by casting, molding, or deposition, or any other means. A single mold in the art of injection molding generally produces a monolithic product. The locking member portions of fill needle hub 502' and fill needle sheath 503' may in particular be integrally molded. This includes in particular spring-loaded members 920*a* and 920*b*.

Figure 11:
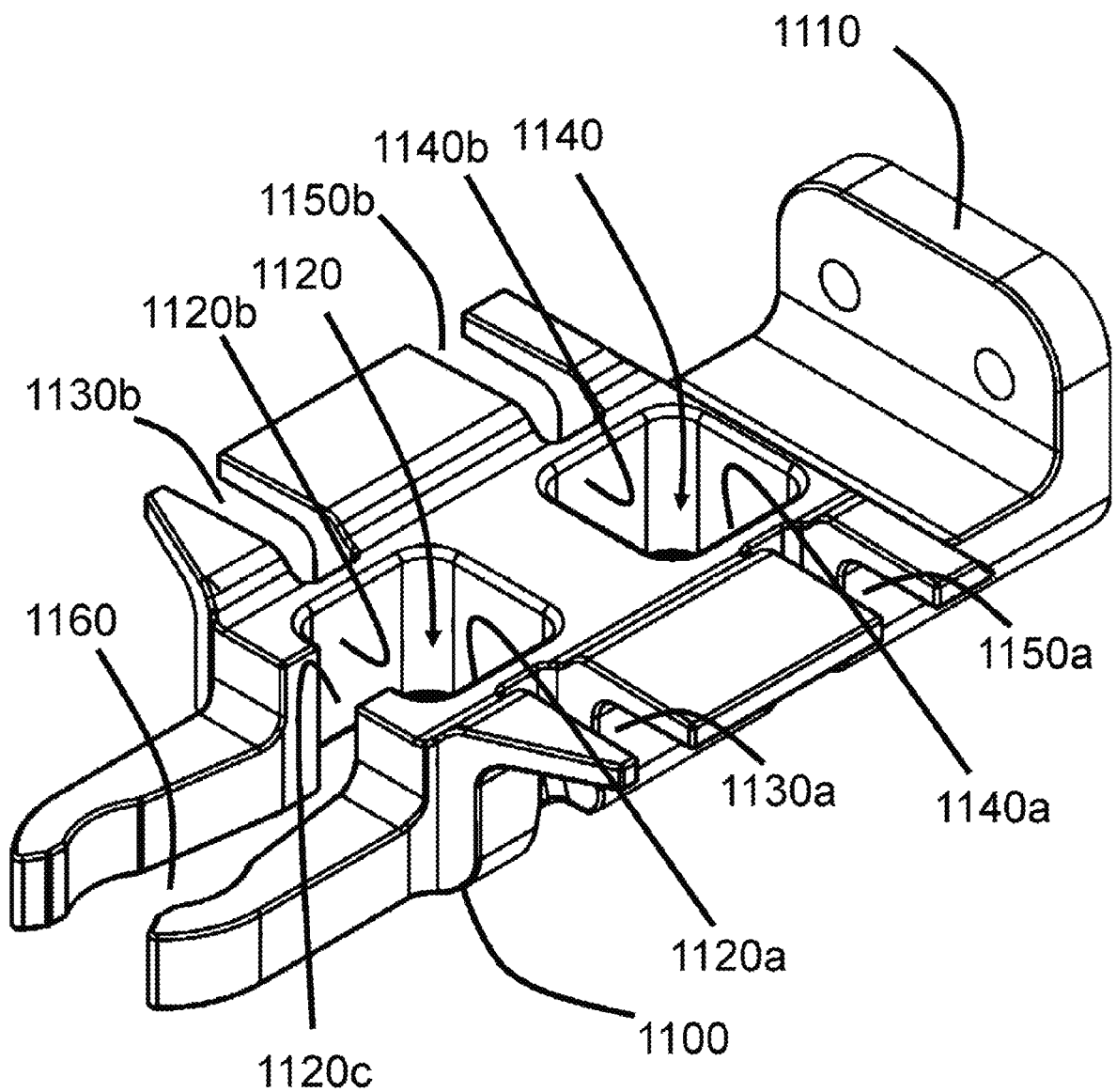
FIG. 11 shows a robotic arm end piece according to one embodiment of the invention for use with for use with the sheath removal station of FIG. 12 and the fill needle and fill needle sheath of FIG. 9A and FIG. 9B.

Fill needle hub 502' comprises two engagement clips 510*a*' and 510*b*' for engaging with robotic arm end piece 1100 of FIG. 11. The operation of these will be described below at the hand of FIG. 11. Engagement clips 510*a*' and 510*b*' are able to flex such that their top ends may be deflected closer together while engagement clips 510*a*' and 510*b*' may push back in reaction against whatever bodies are pushing them together. To this end engagement clips 510*a*' and 510*b*' may be spring loaded. In the embodiment of fill needle hub 502' shown in FIGS. 9A and 9B, engagement clips 510*a*' and 510*b*' are flexible by virtue of being manufactured from an elastic material such as, for example without limitation, a suitable polymeric material compatible with aseptic handling requirements. Engagement clips 510*a*' and 510*b*' are shaped to both clip over robotic arm end piece 1100 of FIG. 11 and be deflected toward each other by end piece 1100.

In the embodiment shown in FIG. 9A and FIG. 9B, fill needle hub 502' is shown as comprising several interior substructures. This approach allows the same mold to be employed for the manufacture by injection molding of all fill needle hubs, while the interior substructures are then adapted to differently sized fill needle tubing 501'. This allows costs to be kept low. Other arrangements of substructures are also contemplated, including without limitation embodiments wherein the entire fill needle hub 502' is one monolithic entity fashioned by injection molding of a suitable polymeric material compatible with aseptic requirements. Based on the above, fill needle package 900 comprises first and second sheath portions that together define a sealed cavity that aseptically encapsulates an implement portion when first and second locking mechanism portions are mutually mated.

In view of the above, flow path 404 of FIG. 1, as supplied for use in this embodiment, comprises flexible tubing 405, an aseptically sealing flange for aseptically sealing flow path 404 to controlled environment chamber 420, and aseptically sealed fill needle package 900.

Figure 9C:
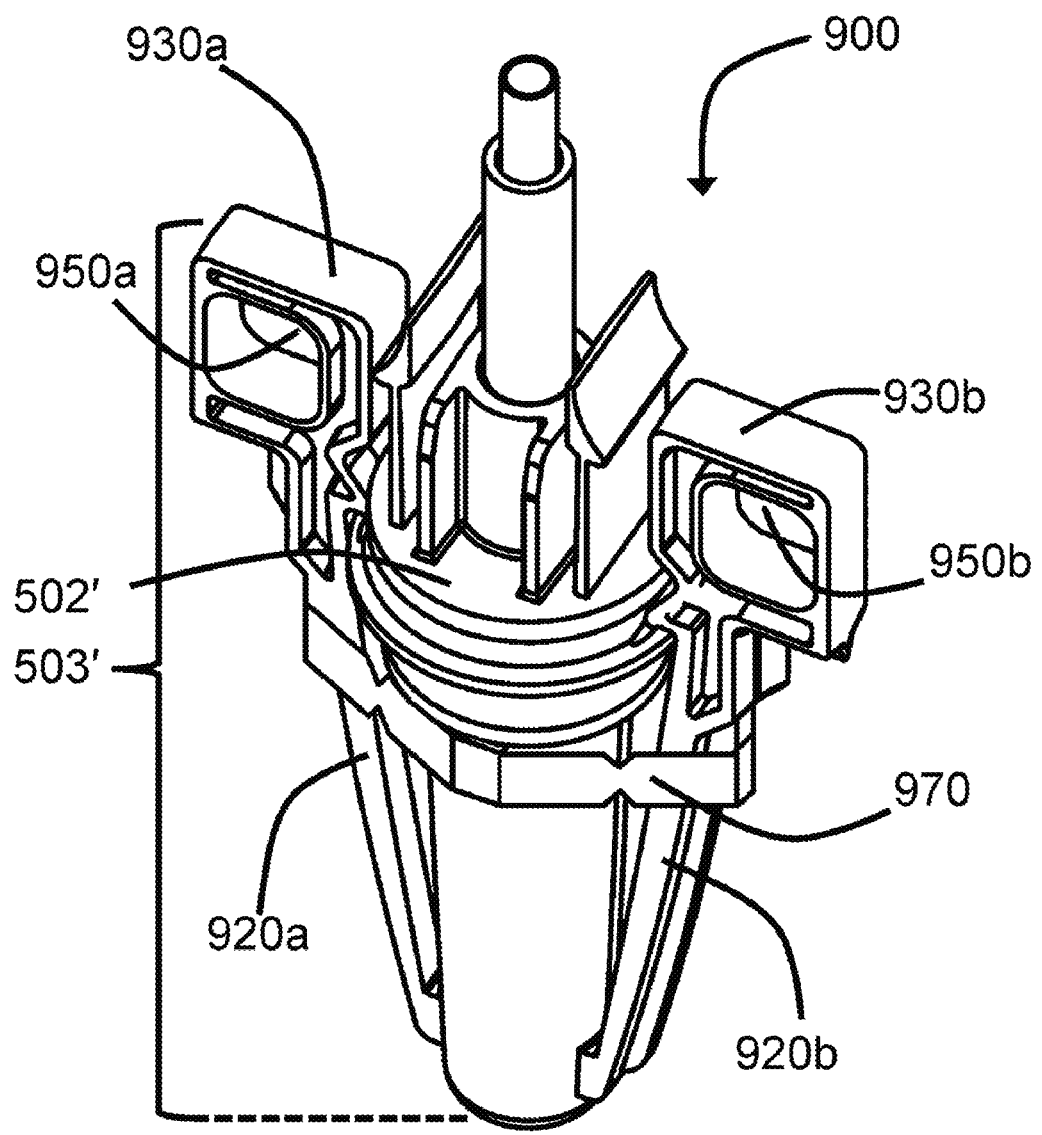
FIG. 9C shows the combination of a fill needle and a fill needle sheath with a tamper-indicator.

Turning now to FIG. 9C, aseptically sealed fill needle package 900 may have tamper indicator 970 that is mechanically linked to one of the locking mechanism portions of fill needle package 900. In FIG. 9C tamper indicator 970 comprises a tearable strip across spring loaded members 920*a* and 920*b*. When locating eyelets 950*a* and 950*b* are forced apart, the portion of tamper indicator 970 disposed across spring loaded members 920*a* and 920*b* is torn irreversibly. Since the same act of separating locating eyelets 950*a* and 950*b* also leads to the separation of sealing surfaces between fill needle hub 502' and fill needle sheath 503', the breaking of tamper indicator 970 is a direct indicator of the breach of the aseptic seal between fill needle hub 502' and fill needle sheath 503'. The same tamper-evident arrangement may be made for the swab system described below.

Figure 10:
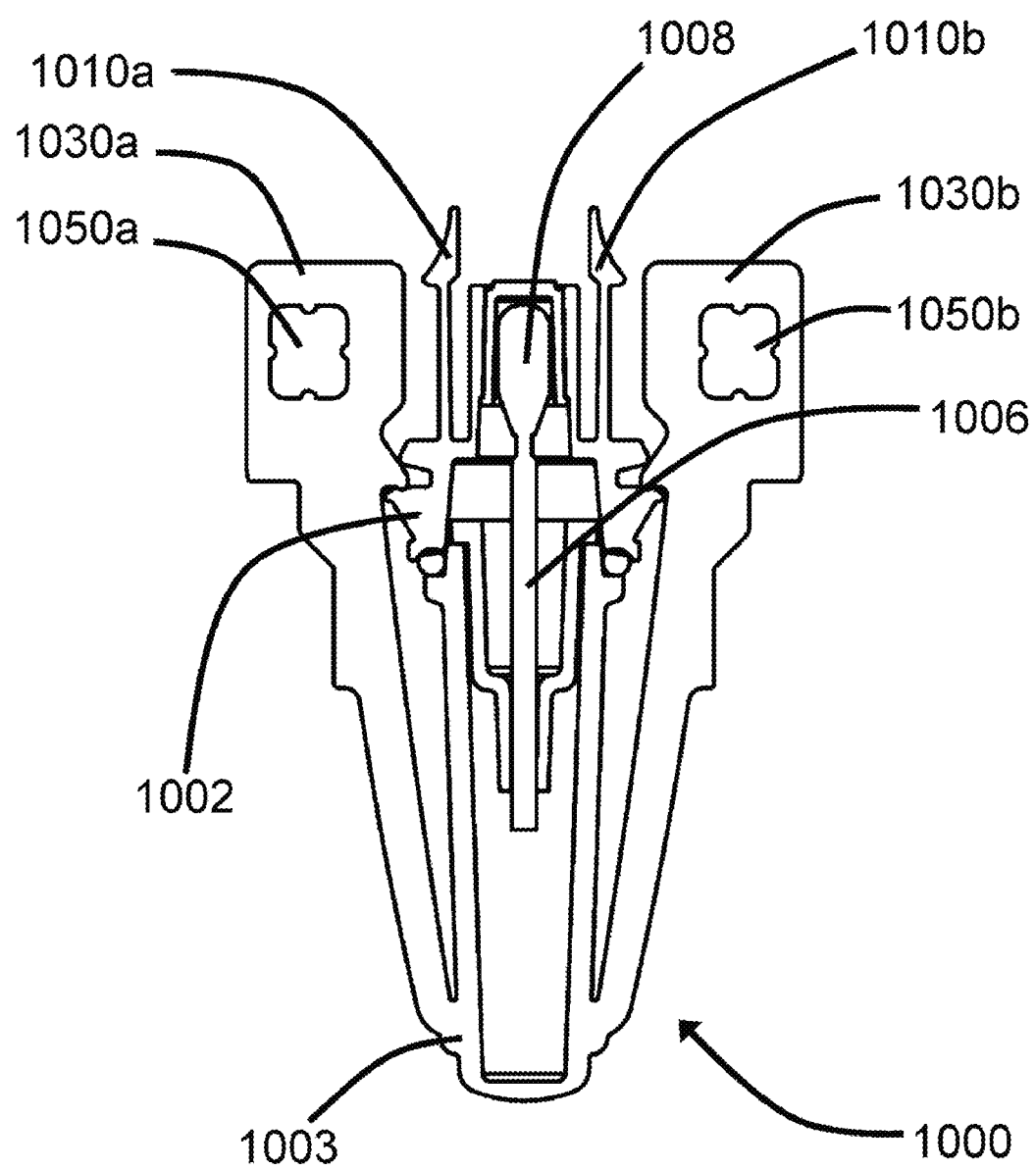
FIG. 10 shows a swab, swab sheath, and swab sheath cap for use with the sheath removal station of FIG. 12 and robotic arm end piece of FIG. 11.

As part of the process of filling a pharmaceutical container with a pharmaceutical product, a regulatory requirement may exist in some cases for the dispensing tip of fill needle 414, 414' to be swabbed with a suitable swab to collect potential contamination species. Such swabs are then typically evaluated by a suitably qualified laboratory in order to assess the aseptic state of the pharmaceutical dispensing process. To this end, in another aspect of the invention, an aseptically sealable/unsealable swab subsystem is provided. In FIG. 10, swab subsystem 1000 comprises swab holder 1003 that may usefully be of the same design as fill needle sheath 503' of FIG. 9A and FIG. 9B. Swab 1006 is mounted within swab holder 1003 with collection tip 1008 of swab 1006 protruding above the top of swab holder 1003. This arrangement allows the dispensing tip of the fill needle 414, 414' to be swabbed by touching the dispensing tip to collection tip 1008 of swab 1006. Swab holder 1003 may be a monolithic injection molded polymeric swab holder.

Swab subsystem 1000 further comprises swab holder cap 1002 that may usefully be of the same design as fill needle hub 502' of FIG. 9A and FIG. 9B, with this modification that swab holder cap 1002 has no fill needle tube 502' and that swab holder cap 1002 is instead permanently sealed at the top. As regards all other mechanical operational aspects, fill needle sheath 503' and fill needle 414' combination 900 and swab subsystem 1000 may be identical. For this reason, the mechanical design aspects of swab subsystem 1000 will not be further discussed here. We shall, however, be referring below to engagement clips 1010*a*' and 1010*b*' of swab holder cap 1002 as regards their engagement with robotic arm end piece 1100 of FIG. 11. We shall also be referring below to locating eyelets 1050*a* and 1050*b* disposed in clamping members 1030*a* and 1030*b* respectively as regards their engagement with fingers. The term "aseptically sealed swab package" 1000 will be used in the present specification to describe this combination of mutually aseptically sealed swab holder cap 1002 and swab holder 1003 containing swab 1006. Swab 1006 is supplied for use packaged in the form of aseptically sealed swab package 1000. Based on the above, swab package 1000 comprises first and second sheath portions that together define a sealed cavity that aseptically encapsulates an implement portion when first and second locking mechanism portions are mutually mated. The locking member portions of swab holder cap 1002 and swab holder 1003 may in particular be integrally molded. This includes in particular spring-loaded members of the structure.

FIG. 11 shows one embodiment of endpiece 1100 for robotic arm 415 of FIG. 1 configured to engage with swab subsystem 1000 of FIG. 10 and with fill needle sheath 503' and fill needle 414' combination 900 of FIG. 9A and FIG. 9B. Flange 1110 is disposed and shaped for attaching endpiece 1100 to robotic arm 415 of FIG. 1. Openings 1120 and 1140 are disposed and shaped for holding fill needle 414' and swab holder cap 1004 respectively. In the case of fill needle 414', engagement clips 510*a*' and 510*b*' of fill needle hub 502' engage with end piece engagement surfaces 1120*a* and 1120*b* of endpiece 1100.

Procedurally, fill needle 414' is engaged as follows with endpiece 1100. Endpiece 1100 is moved forward over the part of fill needle tubing 501' that protrudes out of fill needle 414' and any associated section of flow path 404 joined to fill needle tubing 501' until opening 1120 is directly above fill needle 414'. In this process, opening 1120*c* allows endpiece 1100 to negotiate fill needle tubing 501'. Endpiece 1100 may then be lowered such that the bottom edges of engagement surfaces 1120*a* and 1120*b* engage with the sloped portions of engagement clips 510*a*' and 510*b*'. When endpiece 1100 is lowered further, engagement clips 510*a*' and 510*b*' are both flexibly deflected towards each other until engagement surfaces 1120*a* and 1120*b* pass the sloped portions of engagement clips 510*a*' and 510*b*' and engagement clips 510*a*' and 510*b*' snap back to engage their flat surfaces with engagement surfaces 1120*a* and 1120*b* of endpiece 1100. This securely locates fill needle 414' in endpiece 1100. When fill needle 414' is engaged with endpiece 1100, clamping members 930*a* and 930*b* are disposed in slots 1130*a* and 1130*b* respectively so as to render locating eyelets 950*a* and 950*b* accessible.

In the case of swab holder cap 1004, the engagement proceeds in the same fashion, except that there is no fill needle tubing 501' requiring an opening similar to 1120*c*. Endpiece 1100 is simply moved until opening 1140 is directly above swab holder cap 1004, after which endpiece 1100 is lowered such that the flat surfaces of engagement clips 1010*a*' and 1010*b*' engage with surfaces 1140*a* and 1140*b* of opening 1140 in a fashion similar to that described above for engagement clips 510*a*' and 510*b*'. When swab holder cap 1004 is engaged with endpiece 1100, clamping members 1030*a* and 1030*b* are disposed in slots 1150*a* and 1150*b* respectively so as to render locating eyelets 1050*a* and 1050*b* accessible.

When first using fill needle 414, 414' and flow path 404, the product to be dispensed into containers is first run through flow path 404 and fill needle 414, 414' to establish a steady and reliable flow. This initial volume of product may be dispensed into a priming bottle to be disposed of later. Grip 1160 on endpiece 1100 may be employed as a general tool for handling, for example, stoppers for such priming bottles and the like.

Figure 12:
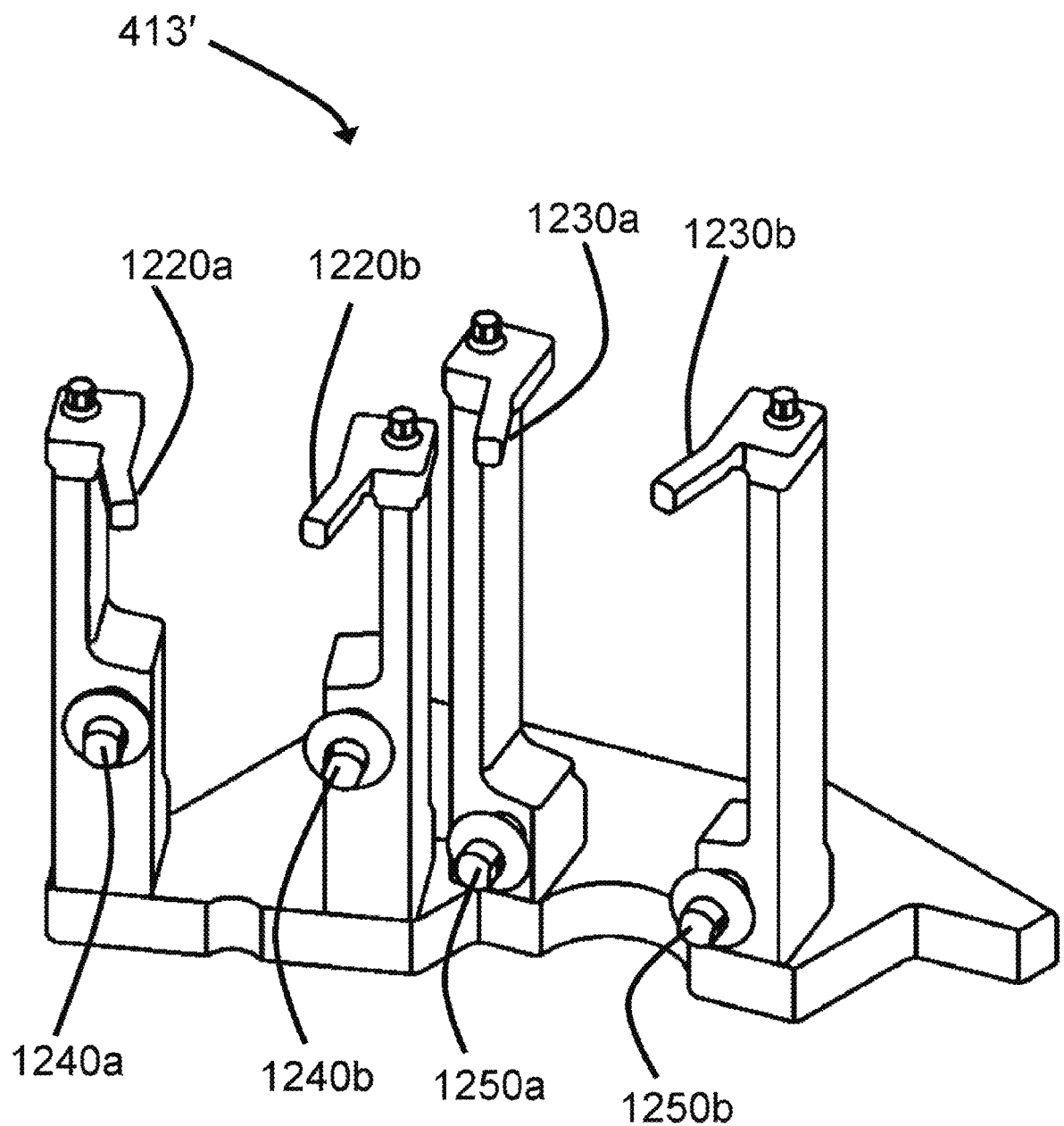
FIG. 12 shows a sheath removal station according to one embodiment of the invention.
Figure 13:
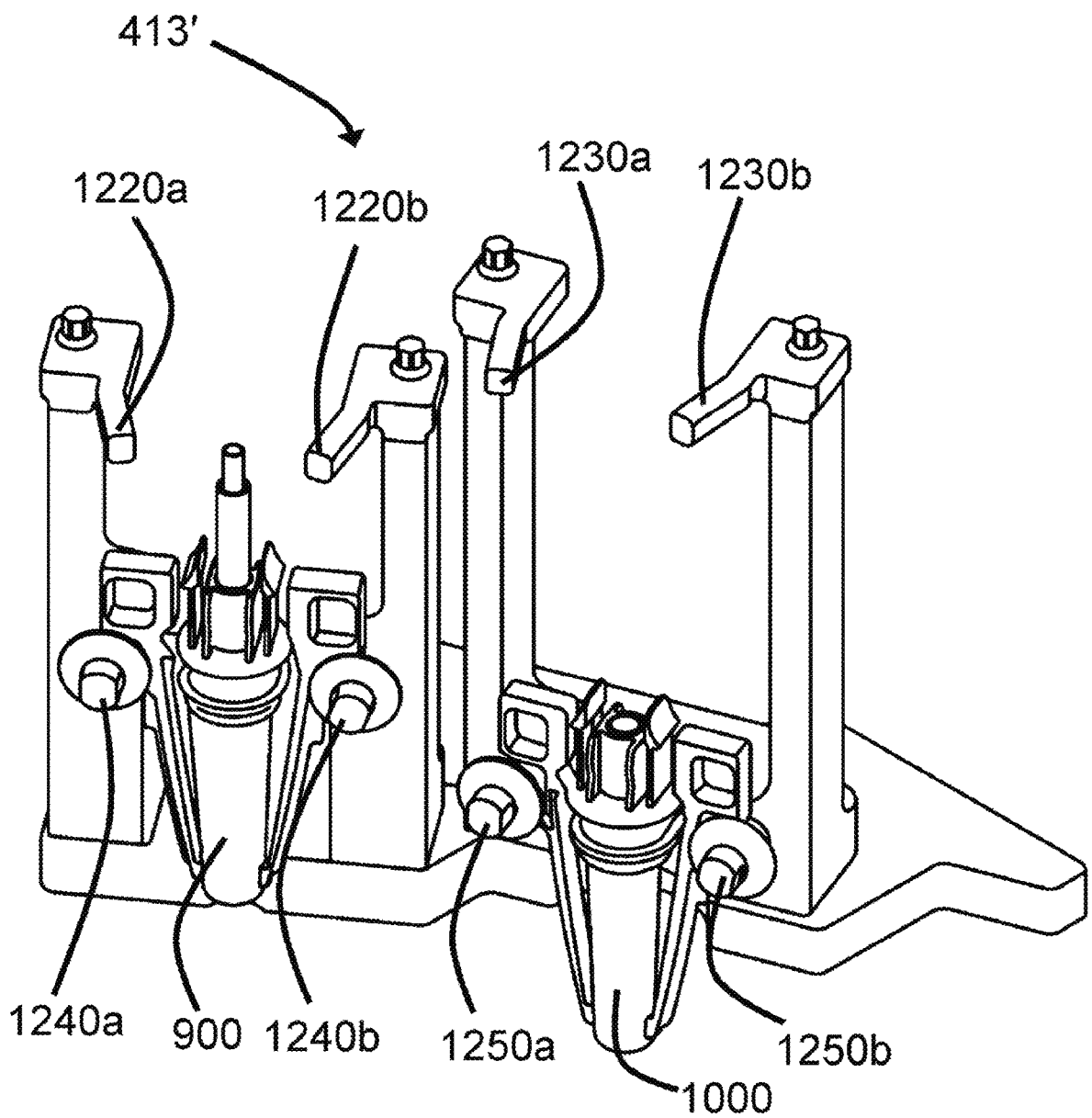
FIG. 13 shows the sheath removal station of FIG. 2 with a swab package and fill needle package suspended on the sheath removal station before use.

To describe the removal of fill needle sheath 503' from fill needle 414', we turn now to FIG. 12, in which sheath removal station 413' comprises sheath engagement fingers 1220*a* and 1220*b* for engaging with locating eyelets 950*a* and 950*b* of fill needle sheath 503'. When fill needle sheath 503', either with or without fill needle 414' engaged with it, is forced onto sheath engagement fingers 1220*a* and 1220*b*, the angled mutual orientation of sheath engagement fingers 1220*a* and 1220*b* forces apart clamping members 930*a* and 930*b* of fill needle sheath 503'. This action forces clamping clips 960*a* and 960*b* apart and disengages clamping clips 960*a* and 960*b* from locating ledge 508' of fill needle hub 502'. O-ring 940 thereby is allowed to expand to its uncompressed state and fill needle 414' is released from fill needle sheath 503'. Fill needle sheath 503' is therefore removably sealable to fill needle 414'. When not in use, fill needle sheath 503' is aseptically sealed to fill needle 414' and may be suspended from suspension stubs 1240*a* and 1240*b* as shown in FIG. 13. As will be described later, an operator may install flow path 404 in chamber 420. In that process, fill needle sheath 503' with fill needle 414' aseptically sealed to it, is positioned on suspension stubs 1240*a* and 1240*b*.

Sheath removal station 413' also comprises sheath engagement fingers 1230*a* and 1230*b* for engaging with locating eyelets 1050*a* and 1050*b* of swab holder 1003. When swab holder 1003, either with or without swab holder cap 1002 engaged with it, is forced onto sheath engagement fingers 1230*a* and 1230*b*, the angled mutual orientation of sheath engagement fingers 1230*a* and 1230*b* forces apart clamping members 1030*a* and 1030*b* of swab holder 1003. This action disengages swab holder cap 1002 from swab holder 1003. Swab holder 1003 is therefore removably sealable to swab holder cap 1002. When not in use, swab holder 1003 aseptically sealed to swab holder cap 1002 may be suspended from suspension stubs 1250*a* and 1250*b* as shown in FIG. 13. As will be described later, at the start of the process of filling pharmaceutical containers with pharmaceuticals in chamber 420, an operator may install swab holder 1003 aseptically sealed to swab holder cap 1002 on suspension stubs 1250*a* and 1250*b* as per FIG. 13.

Figure 14A:
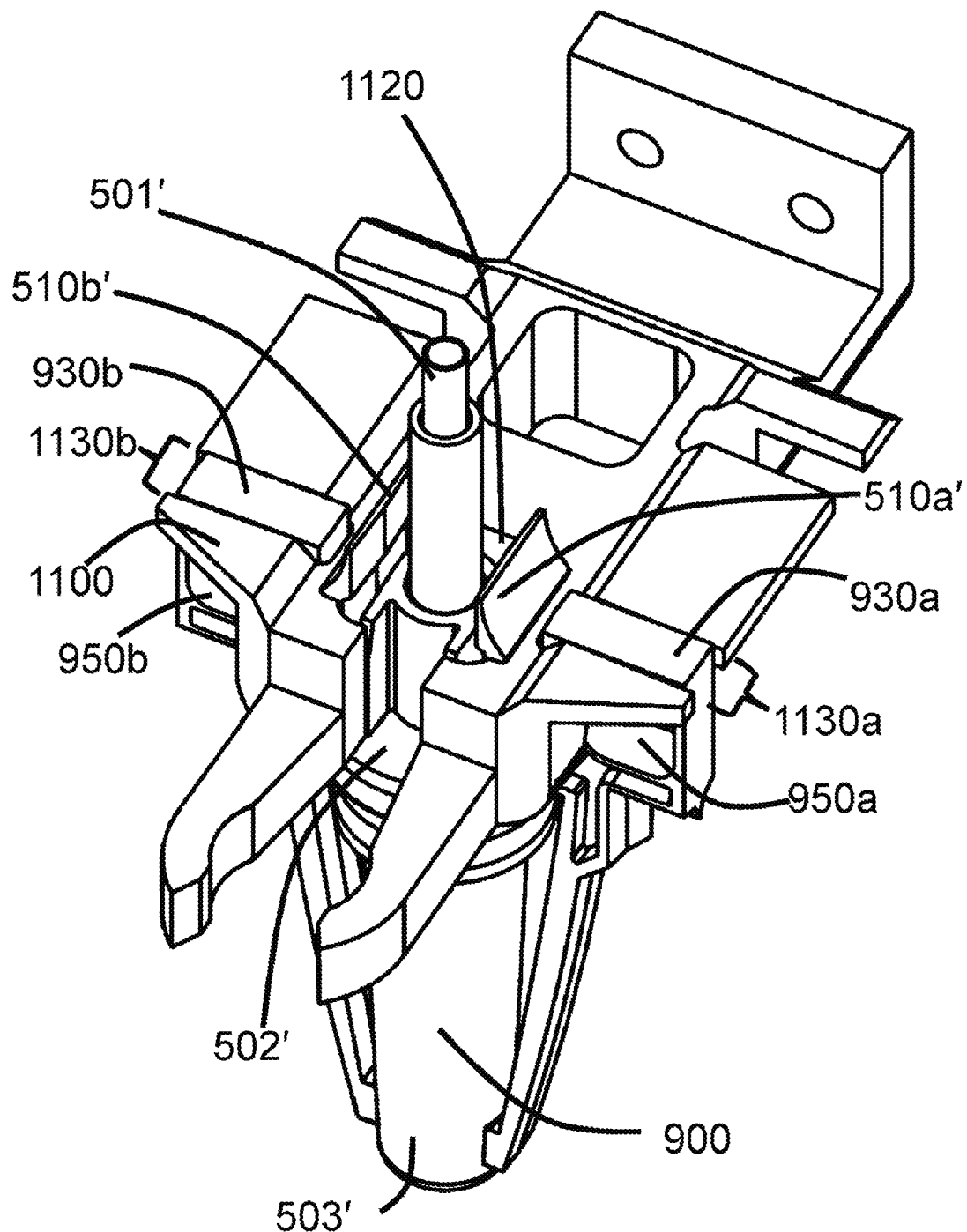
FIG. 14A shows the fill needle package of FIG. 9A and FIG. 9B held by the robotic arm end piece of FIG. 11.
Figure 14B:
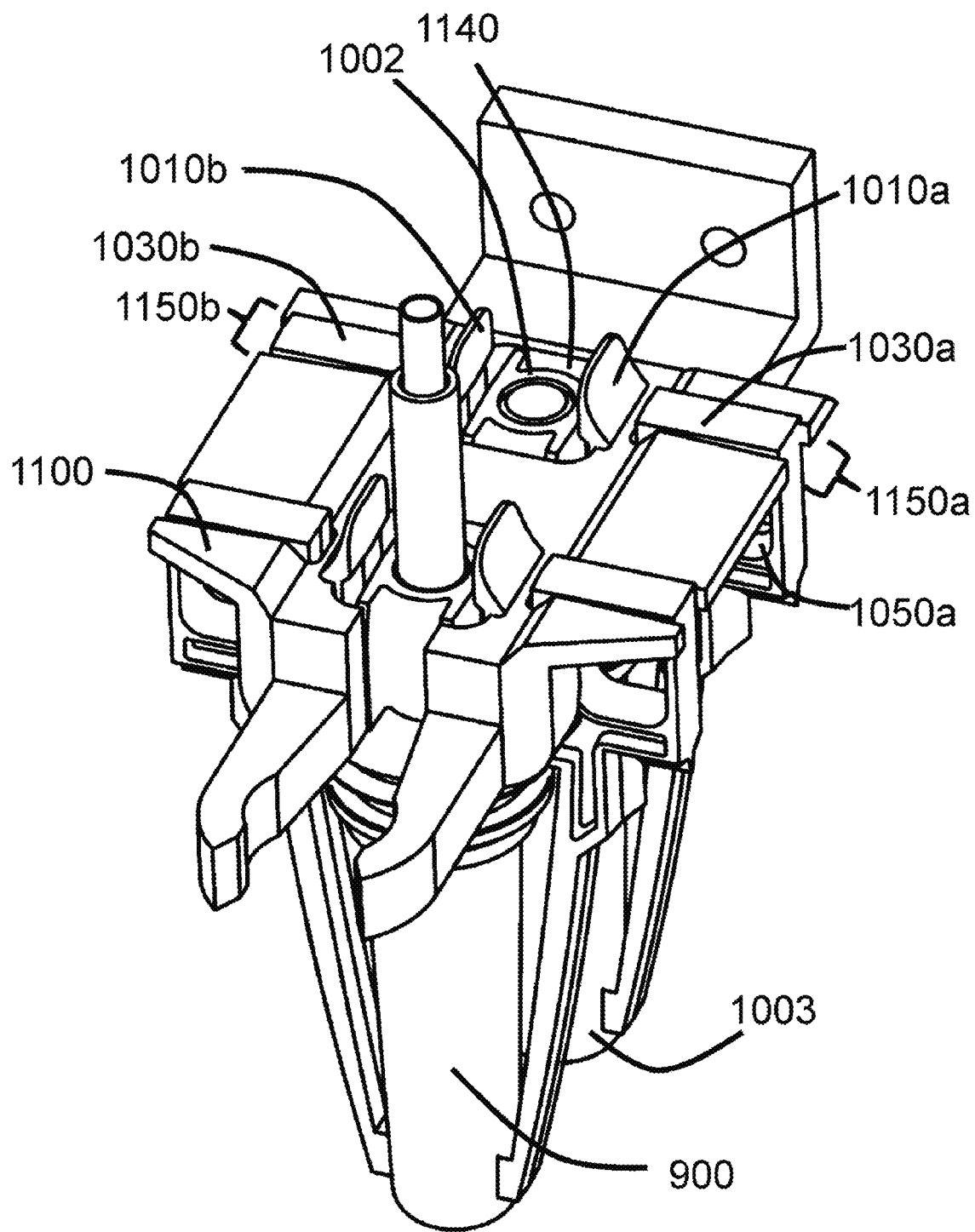
FIG. 14B shows the fill needle package of FIG. 9A and FIG. 9B as well as the swab package of FIG. 10 held by the robotic arm end piece of FIG. 11.

FIG. 14A shows robotic arm endpiece 1100 holding aseptically sealed fill needle package 900 by engagement clips 510*a*' and 510*b*' of fill needle hub 502'. FIG. 14B shows robotic arm endpiece 1100 holding aseptically sealed swab package 1000 by engagement clips 1010*a* and 1010*b* of swab cap 1002.

In operation, fluid path 404 is sealed aseptically to controlled environment enclosure 420 and fill needle package 900 is suspended on suspension stubs 1240*a* and 1240*b* of sheath removal station 413' as shown in FIG. 13. Swab package 1000 is introduced into enclosure 420 and suspended on stubs 1250*a* and 1250*b* of sheath removal station 413' as shown in FIG. 13. Controlled environment enclosure 420 may now be decontaminated using any of the various means previously described. Fluid path may now be unprotected by unsealing fill needle 414' fill needle sheath 503'. This may be done using robotic arm 415 as explained above at the hand of FIG. 12. This step leaves fill needle sheath 503' located on sheath engagement fingers 1220*a* and 1220*b* and fill needle 414' located on robotic arm endpiece 1100.

Swab holder cap 1002 may be similarly removed from swab holder 1003 to expose swab 1006 to the environment in enclosure 420. The process leaves swab holder 1003 with swab 2006 located on sheath engagement fingers 1230*a* and 1230*b* of sheath removal station 413'. Robotic arm 415 now may proceed to fill pharmaceutical vials 411 located on pedestal 412 in FIG. 1 with fluid via fill needle 414'. Fill needle 414' and swab holder cap 1002 remain resident on robotic arm endpiece 1100 during the filling process.

When filling has been completed, robotic arm 415 automatically moves robotic arm endpiece 1100 with fill needle 414' and swab holder cap 1002 to sheath removal station 413' to touch dispensing end 506' of fill needle 414' to exposed tip 1008 of swab 1006.

Using robotic arm 415, eyelets 950*a* and 950*b* of fill needle sheath 503' are engaged with sheath engagement fingers 1220*a* and 1220*b* to allow fill needle 414' to be aseptically sealed to fill needle sheath 503', thereby protecting the fluid path 404. Eyelets 1050*a* and 1050*b* of swab holder 1003 may similarly engage with sheath engagement fingers 1230*a* and 1230*b* of sheath removal station 413' to allow swab holder 1003 and swab holder cap 1002 to be sealed aseptically to each other, thereby protecting swab 2006. Fluid path 404 and sealed swab package 1000 may now be removed from controlled environment enclosure 420.

As shown in FIG. 14B, robotic arm endpiece 1100 has no moving parts and is capable of simultaneously bearing both fill needle package 900 and swab package 1000. Despite both robotic arm endpiece 1100 and sheath removal station 413' having no moving parts, they are jointly capable of opening and closing both fill needle package 900 and swab package 1000. This is possible by virtue of the interaction between the engagement fingers 1220*a*, 1220*b*, 1230*a*, 1230*b* of sheath removal station 413' and eyelets 950*a* and 950*b* of fill needle sheath 503' and eyelets 1050*a* and 1050*b* of swab holder 1003, combined with the spring-loaded or flexible nature of portions of fill needle sheath 503' and swab holder 1003.

Figure 15:
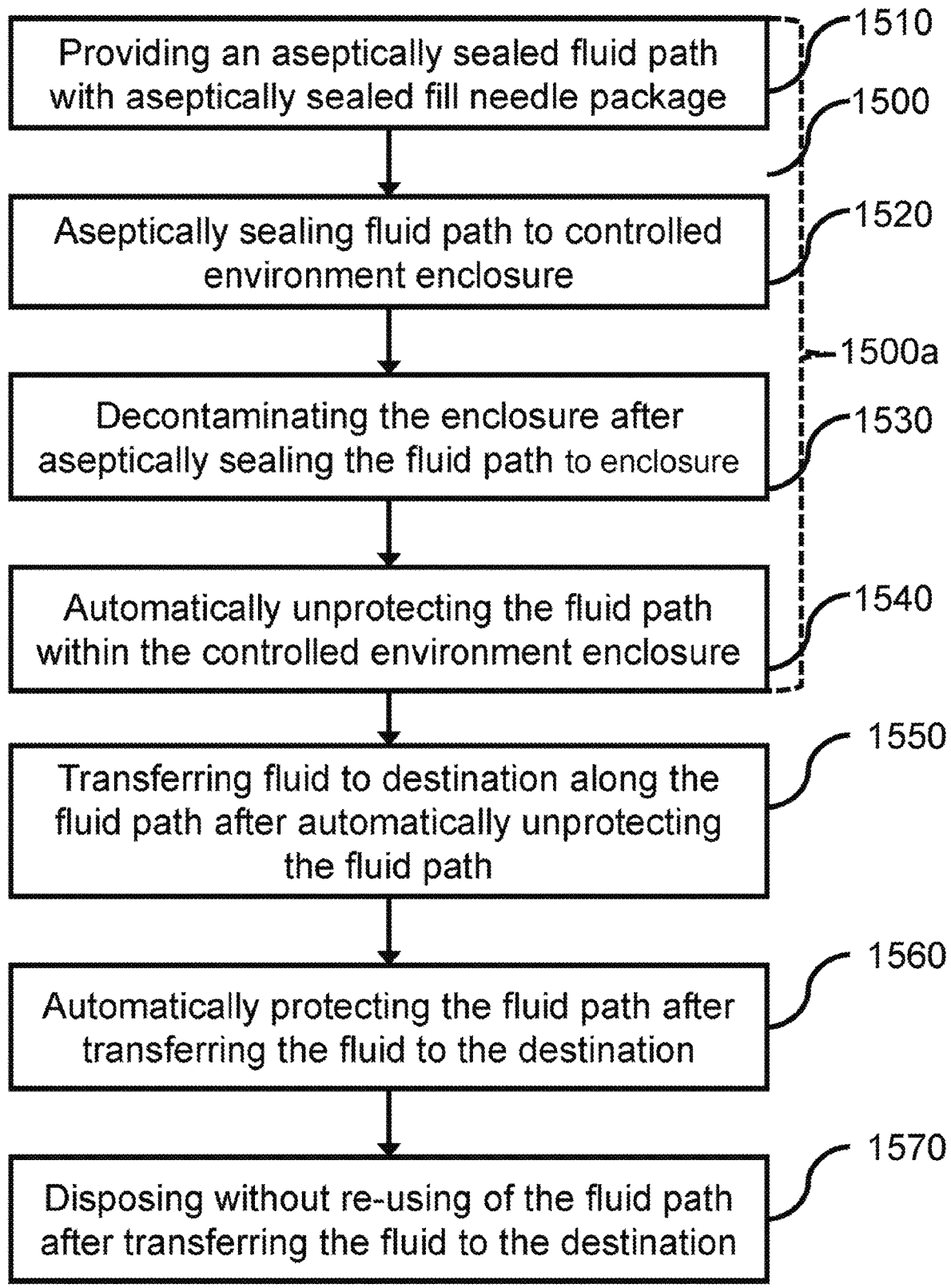
FIG. 15 shows a flow chart of (a) method for transferring within a controlled environment enclosure a fluid along a fluid path to a destination within the controlled environment enclosure and (b) a method for installing a fluid path in the controlled environment enclosure.

In one aspect of the invention, described at the hand of FIG. 15, a method is provided for transferring [1500] within a controlled environment enclosure a fluid along a fluid path to a destination within the controlled environment enclosure, the method comprising providing [1510] an aseptically sealed fluid path comprising an aseptically sealed fill needle package, aseptically sealing [1520] the fluid path to the controlled environment enclosure, decontaminating [1530] the controlled environment enclosure after aseptically sealing the fluid path to the controlled environment enclosure, automatically unprotecting [1540] the fluid path within the controlled environment enclosure, transferring [1550] the fluid to the destination along the fluid path after the automatically unprotecting, and disposing without re-using [1570] of the fluid path after transferring the fluid to the destination.

The automatically unprotecting [1540] may be by automatically operating a robotic arm. The decontaminating [1530] the controlled environment enclosure may automatically be done after the sealing the fluid path to the controlled environment enclosure. The providing an aseptically sealed fluid path [1510] may comprise providing a fill needle removably and aseptically sealed to a fill needle sheath and the sheath may be a monolithic injection molded polymeric fill needle sheath. Providing an aseptically sealed fluid path [1510] may comprise providing a pre-sterilized tube aseptically sealed to the fill needle. Transferring [1550] the fluid to a destination may comprise transferring the fluid to at least one of a culture of cells, a culture of tissue, an enzyme solution, a suspension of immobilized enzymes, a mix of active ingredients, and an excipient. Transferring [1550] the fluid may be transferring an aseptic fluid. Transferring [1550] within a controlled environment enclosure may be transferring within an isolator. The transferring the fluid [1550] to a destination may comprise at least one of transferring the fluid to microwell plates and to containers for pharmaceutical products.

The method may further comprise automatically protecting [1560] the fluid path after transferring the fluid to the destination and before disposing of the fluid path. Transferring [1550] the fluid may comprise filtering the fluid in the fluid path. The filtering may be sterile filtering.

As part of the method described above, a method [1500a] is provided for installing a fluid path within a controlled environment enclosure comprising, providing [1510] an aseptically sealed fluid path comprising an aseptically sealed fill needle package, aseptically sealing [1520] the fluid path to the controlled environment enclosure, decontaminating [1530] the controlled environment enclosure after aseptically sealing the fluid path to the controlled environment enclosure, and automatically unprotecting [1540] the fluid path within the controlled environment enclosure. The automatically unprotecting may be by automatically operating a robotic arm. The decontaminating the controlled environment enclosure may be automatically done after the sealing the fluid path to the controlled environment enclosure. The providing a fill needle may comprise providing a fill needle removably and aseptically sealed to a fill needle sheath. The providing a fill needle may comprise providing a fill needle removably and aseptically sealed to a monolithic injection molded polymeric fill needle sheath.

Figure 16:
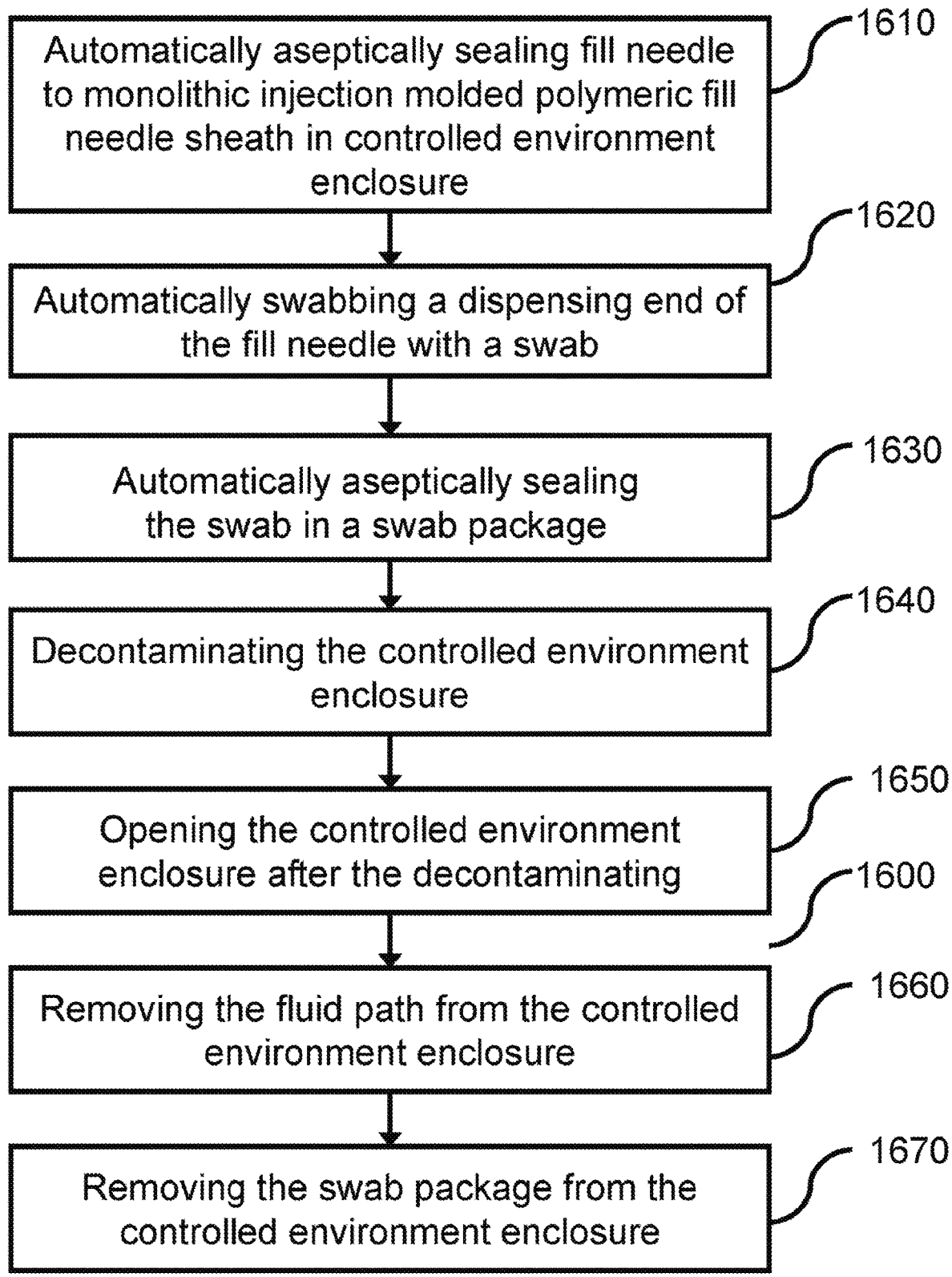
FIG. 16 shows a flowchart of a method for uninstalling from a controlled environment enclosure a fluid path comprising a fill needle.

In a further aspect of the invention described at the hand of FIG. 16, a method is provided for uninstalling [1600] from a controlled environment enclosure a fluid path comprising a fill needle, the method comprising automatically aseptically sealing [1610] the fill needle to a monolithic injection molded polymeric fill needle sheath within the controlled environment enclosure, decontaminating [1640] the controlled environment enclosure after aseptically sealing [1610] the fluid path, opening [1650] the controlled environment enclosure after the decontaminating [1640], and removing [1660] the fluid path from the controlled environment enclosure. The method may further comprise automatically swabbing [1620] a dispensing end of the fill needle with a swab and automatically aseptically sealing the swab [1630] in a swab package before decontaminating [1640] the controlled environment, and removing [1670] the swab package from the controlled environment enclosure after opening the controlled environment enclosure.

Automatically aseptically sealing the fluid path [1610] may be by automatically operating a robotic arm. Decontaminating [1640] the controlled environment enclosure may be done automatically after sealing [1610] the fluid path. Opening [1650] the controlled environment enclosure is done automatically after decontaminating [1640] the controlled environment enclosure. Automatically swabbing [1620] may be by automatically operating a robotic arm. Automatically aseptically sealing [1610] the fluid path may be by automatically operating the robotic arm. Decontaminating [1640] the controlled environment enclosure may be done automatically after sealing the fluid path [1610] and sealing the swab [1630]. Swabbing [1620] may be with a swab disposed in a monolithic injection molded polymeric swab holder.

As part of the above methods, a subsidiary method is provided for decontaminating a controlled environment enclosure containing a fluid path having a fill needle, the method comprising automatically aseptically sealing [1610] the fill needle to a monolithic injection molded polymeric fill needle sheath within the controlled environment enclosure, and decontaminating [1620] the controlled environment enclosure after aseptically sealing [1610] the fluid path. Automatically aseptically sealing [1610] the fluid path may be by automatically operating a robotic arm. A subsidiary method is also provided for decontaminating a controlled environment enclosure containing a swab disposed in a swab holder, the method comprising automatically aseptically sealing the swab holder to a swab holder cap [1630] within the controlled environment enclosure, and decontaminating [1640] the controlled environment enclosure after aseptically sealing the swab holder to a swab holder cap. Automatically aseptically sealing [1630] the swab holder to a swab holder cap may be by automatically operating a robotic arm.

In the above-described embodiments, a pair of injection-molded parts are snapped together using integrally molded leaf spring members with clamping clips that engage with locating ledges. This action provides a positive mechanical detent that ensures that the implement is reliably sealed inside the sheath. But one of ordinary skill in the art would recognize that a variety of other types of mechanisms may be used to provide this type of action, including but not limited to cam-based mechanisms, ratcheting mechanisms, bistable linkages, spring-loaded balls, snaps, and latch pins.

The mechanisms in the above-described embodiments are presented in configurations that allow a concave sheath and cover-like hub to be engaged with each other along a vertical axis, but other geometric configurations may also be implemented. A pair of concave sheath portions could both partly enclose an implement in a downward-facing clamshell-type configuration, for example. And while the sheath and its corresponding hub are preferably manufactured as two completely separate parts as described above, they could also be built as a compound unit, such as by connecting them with a hinge or tether.

The above-described embodiments also provide bearing surfaces on engagement clips and in eyelets that respectively interact with an endpiece on a robot arm and protrusions on a holding station, which allow a robot arm to automatically open and close the sheath. But one of ordinary skill in the art would recognize that many other combinations and arrangements of bearing surfaces could also be employed.

Figure 17:
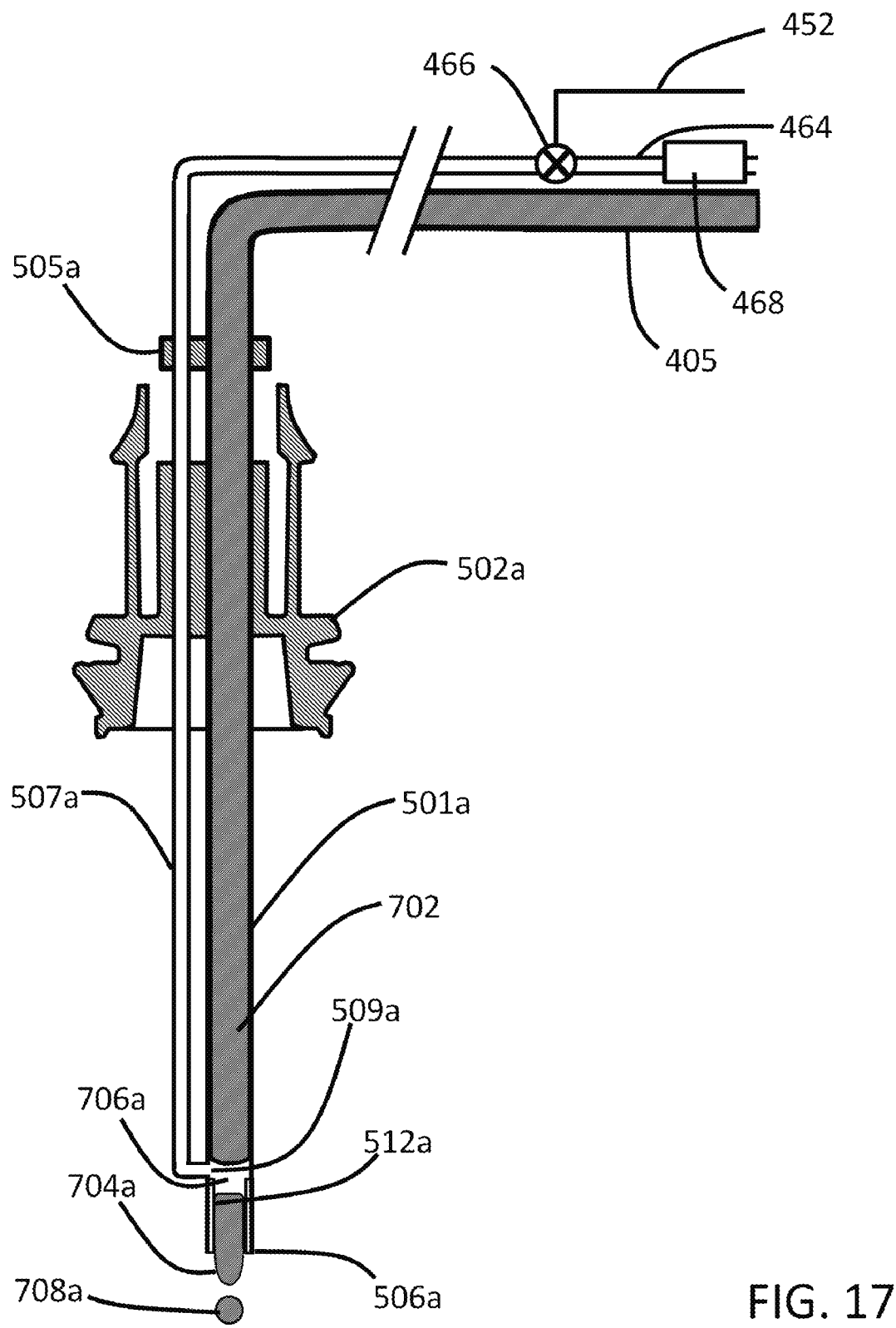
FIG. 17 shows a purgeable fill needle arranged to fit in the kind of fill needle sheath presented in FIG. 9A, FIG. 9B, and FIG. 9C.

In another aspect, a fill needle arrangement shown in FIG. 17 is provided for aseptically dispensing, along fluid path 404 of FIG. 1, pharmaceutical fluid 702 into pharmaceutical container 411 within chamber 420, chamber 420 being capable of maintaining an aseptic condition. In describing the method and associated system, we shall refer to components and subsystems shown in FIG. 1, though the method may apply to other dispensing systems, including the rotary stage filling systems described in co-pending United States Patent Publications US 2018-0072446 A1 (published Mar. 15, 2018), US 2018-0071168 A1 (published Mar. 15, 2018), and US 2018-0282008 A1 (published Oct. 4, 2018), and PCT International Patent Publication WO/2018/049516 (published Mar. 22, 2018), the disclosures of which are hereby incorporated by reference in their entirety. Furthermore, while FIG. 1 shows peristaltic pump 410 as located within aseptic chamber 420, peristaltic pump 410 may be located outside aseptic chamber 420 in order to reduce contamination by moving parts and to limit the extent of locations where biological species may find harbor during sterilization of chamber 420. In describing the method and associated system, we shall refer to fill needle and fill needle sheath arrangements shown in FIGS. 9A, 9B and 9C, though the method may apply to other implementations of fill needles and fill needle sheaths.

FIG. 17 shows an implementation of a purgeable fill needle employing fill needle hub 502a of the same general arrangement as fill needle hub 502' described above at the hand of FIGS. 9A, 9B and 9C, fill needle hub 502a shaped and arranged to mate with a fill needle sheath (not shown in FIG. 17) of the same general arrangement as that of sheath 503' of FIGS. 9A, 9B and 9C. In this implementation, fill needle tubing 501a is provided with gas inlet orifice 509A via which gas may be injected into needle tubing 501a proximate dispensing tip 506a. Gas may be provided through gas tube 507a via gas line 464 from a gas source that may be located outside chamber 420. Needle tubing 501a and gas tube 507a are arranged within fill needle hub 502a such that the combination mates with and fits into a sheath of the same type as sheath 503' in FIGS. 9A, 9B and 9C. Gas line 464 and flexible tubing (see also FIG. 1) are joined to respectively gas tube 507a and fill needle tubing 501a by connector 505a, shown schematically in FIG. 17. As already described, flexible tubing 405 enters chamber 420 (See FIG. 1) via a suitable aseptically sealing flange, so that the exterior of fluid path 404 within chamber 420 is aseptically sealed to the interior of chamber 420. Gas line 464 enters chamber 420 via a suitable aseptically sealing flange (not shown), so that the exterior of gas line 464 within chamber 420 is aseptically sealed to the interior of chamber 420.

At least interior 512a of the terminal region of dispensing tip 506a between the end of fill needle tubing 501a and gas inlet orifice 509A may be at least one of lined with a hydrophobic material, coated with a hydrophobic material, and treated to render it hydrophobic, or may consist of a separate section of hydrophobic tubing. This lowers the ability of water-based or other polar pharmaceutical fluids to stick to the inside wall of dispensing tip 506a. The lowered attraction of such fluids to the interior wall of dispensing tip 506a facilitates the purging of fluid from dispensing tip 506a. The term "hydrophobic" is used in the present specification as being synonymous with "low surface energy".

In operation, when the flow of pharmaceutical fluid through fill needle tubing 501a is halted, an amount of pharmaceutical, shown as 704a in FIG. 17 and referred to in this specification as the "terminal pharmaceutical fluid portion", remains in or attached to dispensing tip 506a. This may be in the form of fluid between the end of fill needle tubing Ola and gas inlet orifice 509A and/or a droplet of pharmaceutical fluid that has remained attached to the fill needle tip. The inventors have found empirically that the action of removing terminal pharmaceutical fluid 704a retained in the proximity of the dispensing end of dispensing tip 506a results in distinctly more repeatable dispensing volumes.

In the fill needle arrangement of FIG. 17, halting of the flow of pharmaceutical fluid via fluid path 404 (represented by tubing portion 405 in FIG. 17) may be followed by injection of a suitable aseptic gas, for example without limitation air or nitrogen, into fill needle tubing 501a via gas tube 507a and gas line 464 to form gas pocket 706a. As the gas flow continues and gas pocket 706a expands toward the end of dispensing tip 506a, terminal fluid 704a is removing from dispensing tip 506a. Removed terminal fluid 704a may be released from the end of dispensing tip 506a in the form of droplets, for example droplet 708a. The gas flow may be turned on and off automatically by means of suitable valve 466 under control of a controller, for example controller 440 of FIG. 1. To this end, valve 466 may be in communication with controller 440 via valve control line 452. The term "terminal fluid ejector" is used in the present specification to describe the arrangement for removing the terminal pharmaceutical fluid portion 704a. Filter 468 in gas line 464 may be employed to filter the gas supplied to gas tube 507a.

The fill needle may be positioned by a robotic arm, which may be an articulated robotic arm of the type shown as articulated robotic arm 415 in FIG. 1. Robotic arm 415 may have an end effector, for example end effector 1100 of FIG. 11, to engage fill needle hub 502', as shown in FIG. 14A. In FIG. 1 the containers 411 are shown as positioned in a tray on pedestal 412. In other embodiments, the containers may be held in a nest and the nest moved by a robotic arm, the robotic arm in some embodiments being an articulated robotic arm. A non-limiting example of such an arrangement is provided in U.S. patent application Ser. No. 15/729,655 in which FIG. 9 of that application shows containers 510 in a nest 500 and nest 500 is moved by an articulated robotic arm 800. Either or both of the container and the fill needle may be moved to ensure that the fill needle dispensing tip 506a is positioned over the container.

Figure 18:
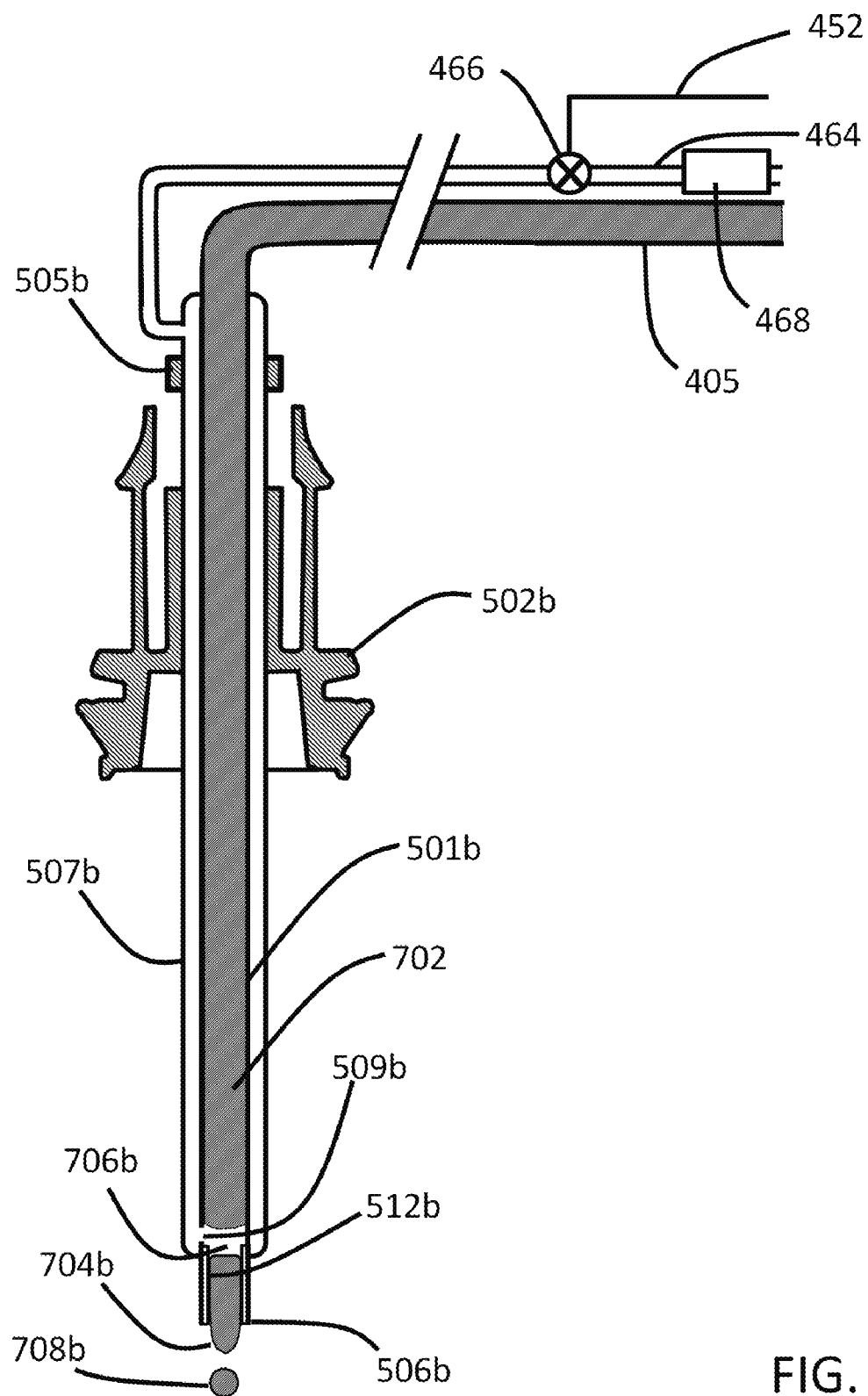
FIG. 18 shows another implementation of a purgeable fill needle arranged to fit in the kind of fill needle sheath presented in FIG. 9A, FIG. 9B, and FIG. 9C.

FIG. 18 shows another embodiment of a purgeable fill needle employing fill needle hub 502b of the same general arrangement as fill needle hub 502' described above at the hand of FIGS. 9A, 9B and 9C, fill needle hub 502b shaped and arranged to mate with a fill needle sheath (not shown in FIG. 18) of the same general arrangement as that of sheath 503' of FIGS. 9A, 9B and 9C. It differs from the embodiment shown in FIG. 17 in that the gas is channeled along annular sheath 507b around fill needle tubing 501b. The term "gas channel" is used in the present specification to describe both annular sheath 507b of FIG. 18 and gas tube 507a of FIG. 17. The gas then enters fill needle tubing 501b at gas inlet orifice 509B to form gas pocket 706b. As in the embodiment of FIG. 17, terminal pharmaceutical fluid portion 704b is forced out of dispensing tip 506b in the form of droplets, for example droplet 708b. At least interior 512b of the terminal region of dispensing tip 506b between the end of fill needle tubing 501*b* and gas inlet orifice 509B may be at least one of lined with a hydrophobic material, coated with a hydrophobic material, and treated to render it hydrophobic, or may consist of a separate section of hydrophobic tubing. As with the embodiment in FIG. 17, the term "terminal fluid ejector" is used in the present specification to describe the arrangement of elements for removing the terminal pharmaceutical fluid portion 704*b*. Gas line 464 and flexible tubing 405 (See FIG. 1) are joined to respectively tube 507*b* and fill needle tubing 501*b* by connector 505*b*, shown schematically in FIG. 18. Filter 468 in gas line 464 may be employed to filter the gas supplied to annular sheath 507*b*.

Whereas the fill needle implementations in both FIG. 17 and FIG. 18 are configured for mating with sheaths of the type 503' in FIGS. 9A, 9B and 9C, they may be employed with any other suitable sheathing arrangement, including but not limited to that of FIG. 2.

Figure 19:
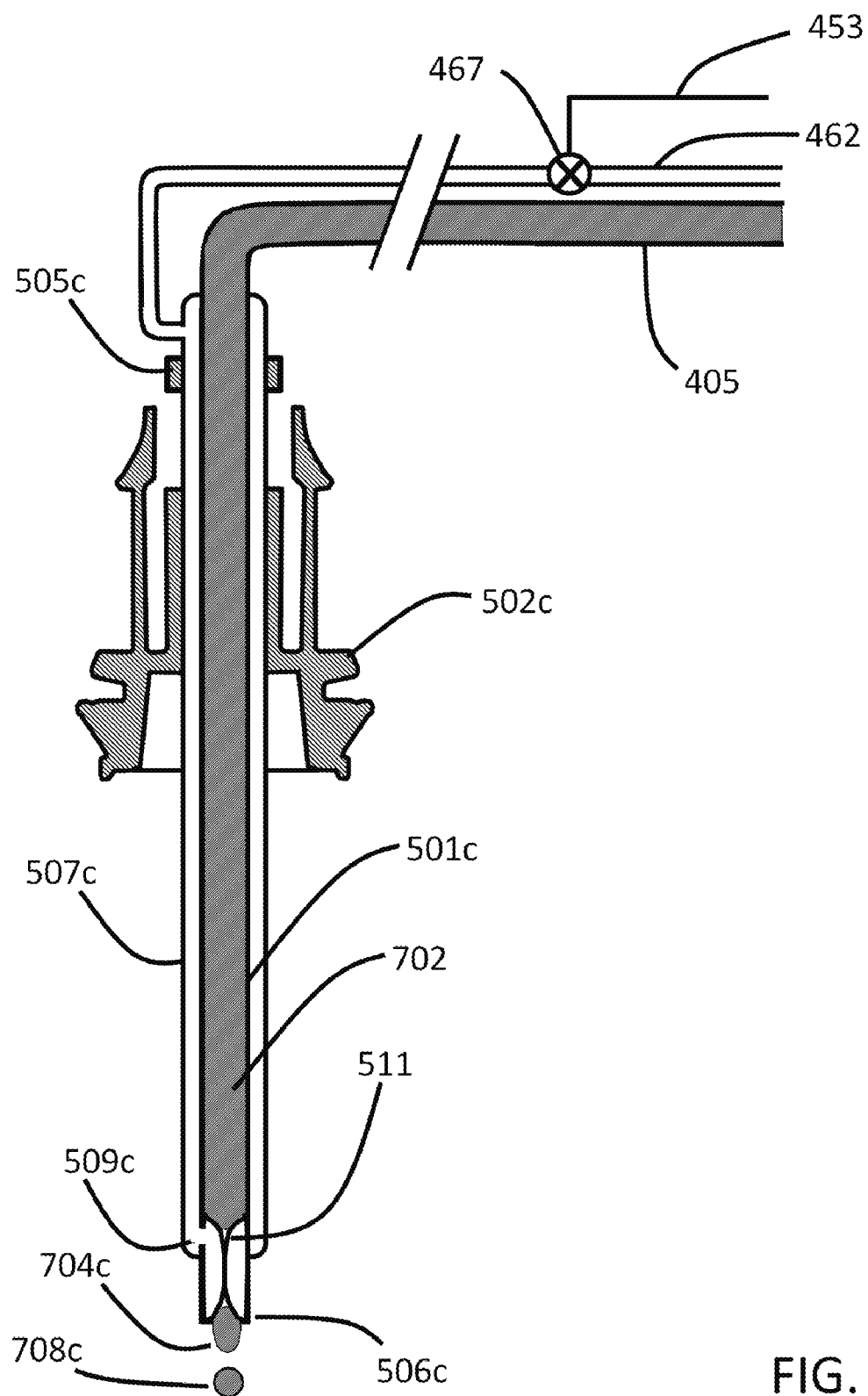
FIG. 19 shows another implementation of a purgeable fill needle arranged to fit in the kind of fill needle sheath presented in FIG. 9A, FIG. 9B, and FIG. 9C.

FIG. 19 shows another embodiment of a purgeable fill needle employing fill needle hub 502*c* of the same general arrangement as fill needle hub 502' described above at the hand of FIGS. 9A, 9B and 9C, fill needle hub 502*c* shaped and arranged to mate with a fill needle sheath (not shown in FIG. 18) of the same general arrangement as that of sheath 503' of FIGS. 9A, 9B and 9C. Dispensing tip 506*c* is configured to produce droplets 708*c* of pharmaceutical fluid 702. In this embodiment, dispensing tip 506*c* comprises inflatable annular bladder 511, which may be pneumatically inflated or deflated by controlling the gas pressure in bladder 511. As in the embodiment of FIG. 18, the gas pressure may be controlled by controller 440 via control line 453 to valve 467. Valve 467 may, for example, inflate bladder 511 by injecting gas from gas line 462 via annular gas channel 507*c* and through gas inlet orifice 509C. Conversely, valve 467 may, for example, deflate bladder 511 by releasing gas from annular gas channel 507*c*. When annular bladder 511 is inflated, terminal pharmaceutical fluid portion 704*c* may be pneumatically removed from dispensing tip 506'*c*. As with the embodiment of FIG. 18, dispensing tip 506*c* may be at least in part lined with a hydrophobic material, coated with a hydrophobic material, or treated to render it hydrophobic. As with the embodiments in FIG. 17 and FIG. 18, the term "terminal fluid ejector" is used in the present specification to describe the arrangement of elements for removing the terminal pharmaceutical fluid portion 704*c*.

Gas line 462 and flexible tubing 405 (See also FIG. 1) are joined to respectively annular gas channel 507*c* and fill needle tubing 501*c* by connector 505*c*, shown schematically in FIG. 19. Gas line 462 enters chamber 420 via a suitable aseptically sealing flange (not shown), so that the exterior of gas channel 507*c* and the exterior of the gas line 462 within chamber 420 are aseptically sealed to the interior of chamber 420. In operation, the gas employed in the embodiment of FIG. 19 does not come into direct contact with the pharmaceutical fluid as long as the bellows retain integrity, and is not subject to the same sterility requirements as the gas employed in the embodiments of FIG. 17 and FIG. 18.

Figure 20:
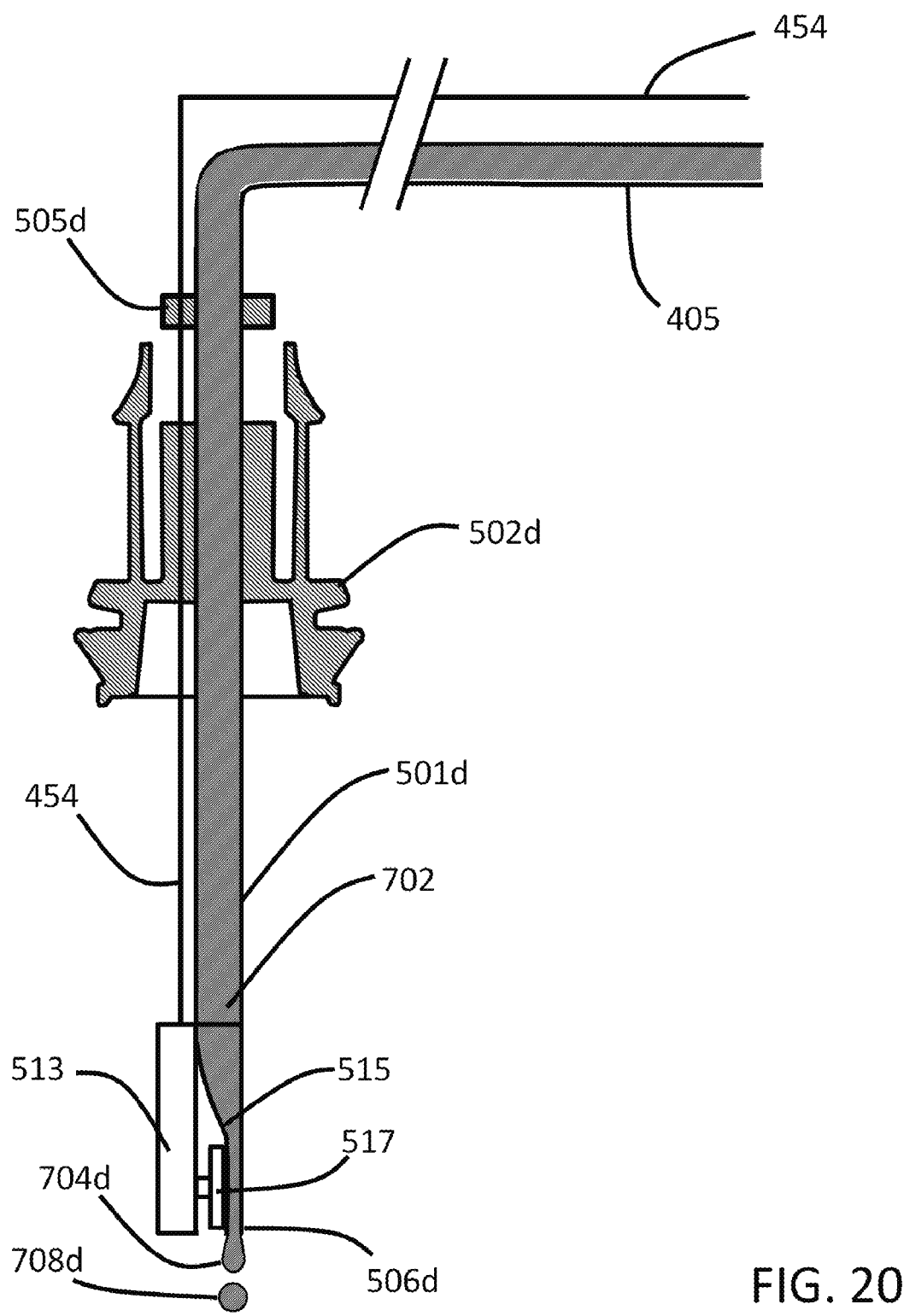
FIG. 20 shows an implementation of a purgeable fill needle employing a compression actuator for removing fluid from a dispensing tip of the needle.

FIG. 20 shows another embodiment of a purgeable fill needle employing fill needle hub 502*d* of the same general arrangement as fill needle hub 502' described above at the hand of FIGS. 9A, 9B and 9C, fill needle hub 502*d* shaped and arranged to mate with a fill needle sheath (not shown in FIG. 18) of the same general arrangement as that of sheath 503' of FIGS. 9A, 9B and 9C. Flexible tubing 405 (see also FIG. 1) is joined to fill needle tubing 501*d* by connector 505*d*, as shown schematically in FIG. 19. Dispensing tip 506*d* is configured to produce droplets 708*d* of pharmaceutical fluid 702. In this embodiment, dispensing tip 506*d* internally comprises a flexible terminal tube 515 attached to fill needle tubing 501*d* and compression actuator 513 configured for driving a compression element 517 to compress flexible terminal tube 515 in order to remove terminal pharmaceutical fluid portion 704*d*. Controller 440 may control actuator 513 via control line 454. Control line 454 may pass connectably through connector 505*d*. This allows terminal pharmaceutical fluid portion 704*d* to be automatically removed without direct operator intervention. Flexible terminal tube 515 may be at least in part lined with a hydrophobic material, coated with a hydrophobic material, or treated to render it hydrophobic. Flexible terminal tube 515 may be made from a hydrophobic material.

Several arrangements for actuator 513 may be implemented. In one embodiment, compression actuator 513 may be piezoelectrically driven. Levered piezoelectric actuators are capable of displacements of the order of 1 millimeter which is sufficient displacement for compression element 517 of actuator 513. In other embodiments, actuator 513 may be electromechanically driven. In both these embodiments, compression element 517 may be driven by a suitable armature or lever structure (not shown) within actuator 513. Both kinds of actuators are well known in the art and are not discussed here in more detail. As with the embodiments in FIG. 17, FIG. 18, and FIG. 19, the term "terminal fluid ejector" is used in the present specification to describe the arrangement of elements for removing the terminal pharmaceutical fluid portion 704*d*.

Figure 21:
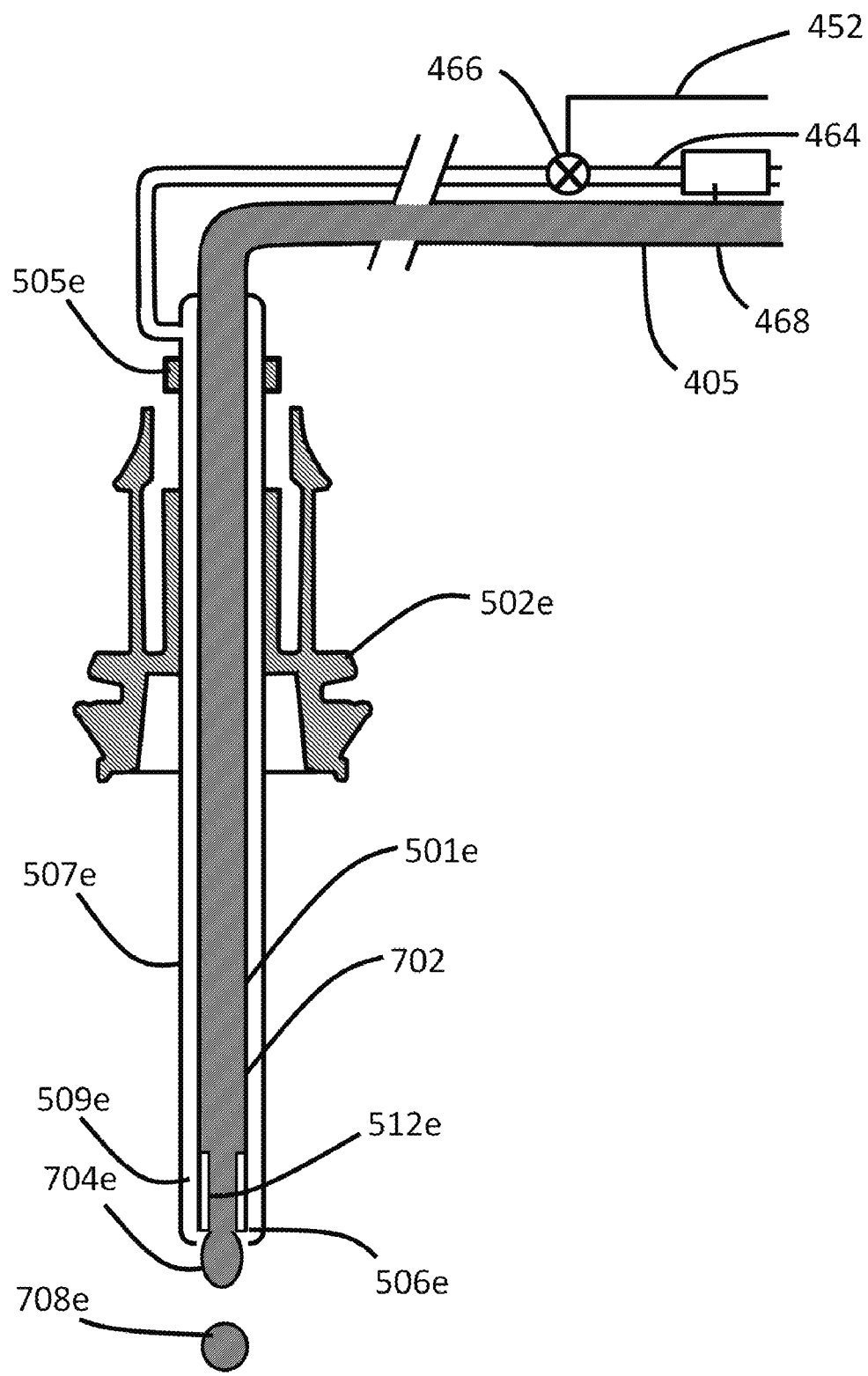
FIG. 21 shows an implementation of a purgeable fill needle employing annularly directed gas to blow droplets of fluid from a dispensing tip of the needle.
Figure 22:
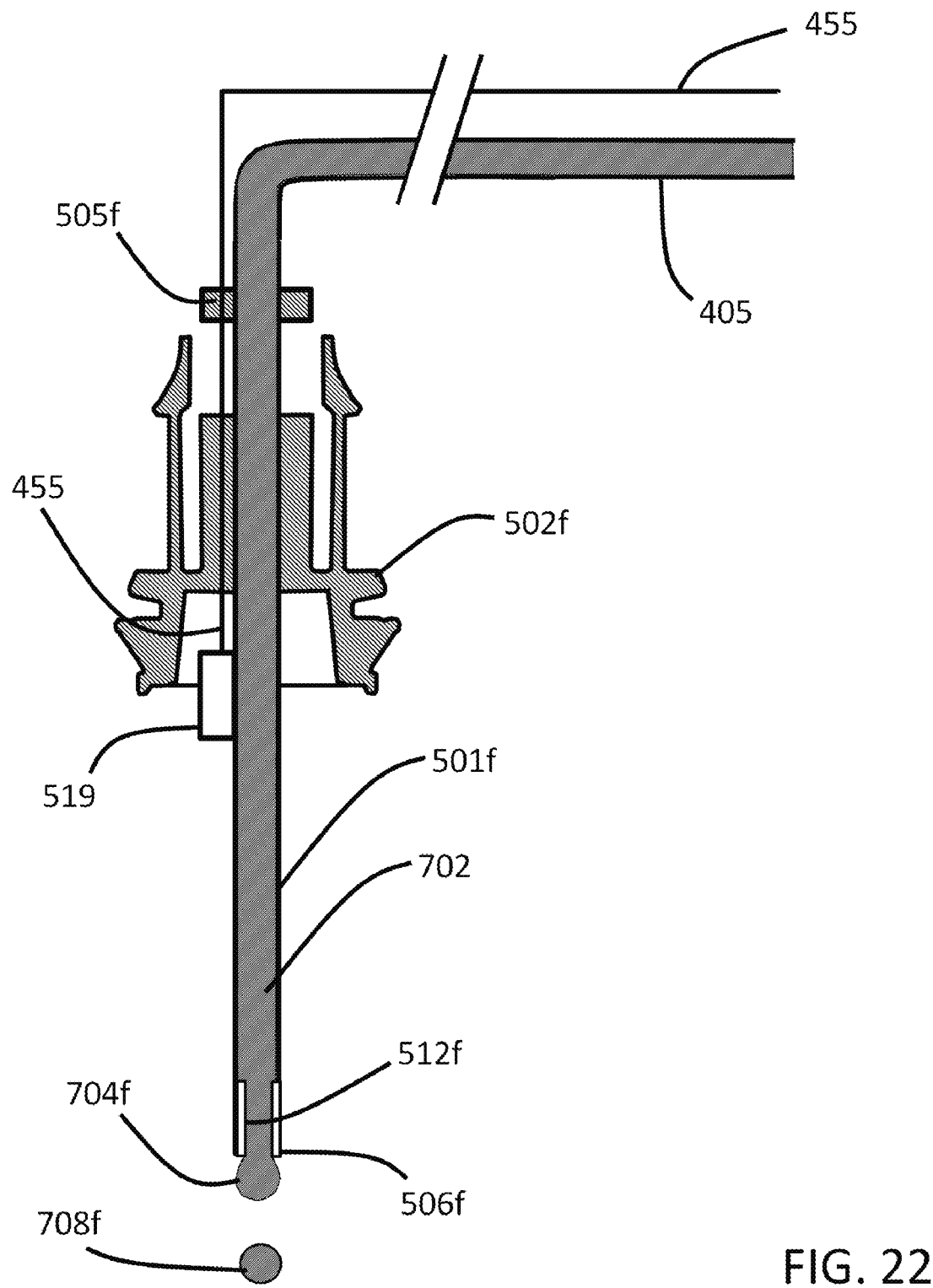
FIG. 22 shows an implementation of a purgeable fill needle employing a vibration actuator for shaking attached droplets of fluid from a dispensing tip of the needle.

FIGS. 21 and 22 show two implementations in which the terminal pharmaceutical fluid portion is substantially composed of a single droplet of pharmaceutical fluid that remains attached to the dispensing tip of the fill needle after halting the dispensing of fluid. FIG. 21 shows a variant of the embodiment presented in FIG. 18 in which only the dispensing end of the fill needle differs from that shown in FIG. 18. In FIG. 21 a purgeable fill needle employs fill needle hub 502*e* of the same general arrangement as fill needle hub 502' described above at the hand of FIGS. 9A, 9B and 9C, fill needle hub 502*e* shaped and arranged to mate with a fill needle sheath (not shown in FIG. 21) of the same general arrangement as that of sheath 503' of FIGS. 9A, 9B and 9C. Gas is channeled along annular sheath 507*e* around fill needle tubing 501*e*. The term "gas channel" is used in the present specification to describe annular sheath 507*e*. The gas then be directed across the outlet of fill needle tubing 501*e* via annular gas outlet orifice 509B to blow the droplet forming terminal pharmaceutical fluid portion 704*e* off dispensing tip 506*e* in the form of unattached droplets, for example droplet 708*e*. At least interior 512*e* of the terminal region of dispensing tip 506*e* may be lined with a hydrophobic material, coated with a hydrophobic material, or treated to render it hydrophobic, or may consist of a separate section of hydrophobic tubing. The term "terminal fluid ejector" is used in the present specification to describe the arrangement of elements for removing the terminal pharmaceutical fluid portion 704*e*. Gas line 464 and flexible tubing 405 (See FIG. 1) are joined to respectively tube 507*e* and fill needle tubing 501*e* by connector 505*b*, shown schematically in FIG. 21. Filter 468 in gas line 464 may be employed to filter the gas supplied to annular sheath 507*e*.

In another embodiment shown in FIG. 22 a purgeable fill needle employs fill needle hub 502*f* of the same general arrangement as fill needle hub 502' described above at the hand of FIGS. 9A, 9B and 9C, fill needle hub 502*f* shaped and arranged to mate with a fill needle sheath (not shown in FIG. 22) of the same general arrangement as that of sheath 503' of FIGS. 9A, 9B and 9C. Actuator 519 is disposed to vibrate fill needle tubing 501e to remove from dispensing tip 506f terminal pharmaceutical fluid portion 704f which, in this case, is droplet 704f. This then produces independent droplets, for example droplet 708f. At least interior 512f of the terminal region of dispensing tip 506f may be at least one of lined with a hydrophobic material, coated with a hydrophobic material, and treated to render it hydrophobic, or may consist of a separate section of hydrophobic tubing. The term "terminal fluid ejector" is used in the present specification to describe the arrangement of elements for removing terminal pharmaceutical fluid portion 704f. Controller 440 may control actuator 519 via control line 455. This allows terminal pharmaceutical fluid portion 704f to be automatically removed without direct operator intervention. Actuator 519 may be actuated on any suitable basis, including without limitation electromechanically and piezolectrically. Flexible tubing 405 (See also FIG. 1) is joined to respectively fill needle tubing 501e by connector 505f, shown schematically in FIG. 21. Control line 455 may pass connectably through connector 505f.

Figure 23:
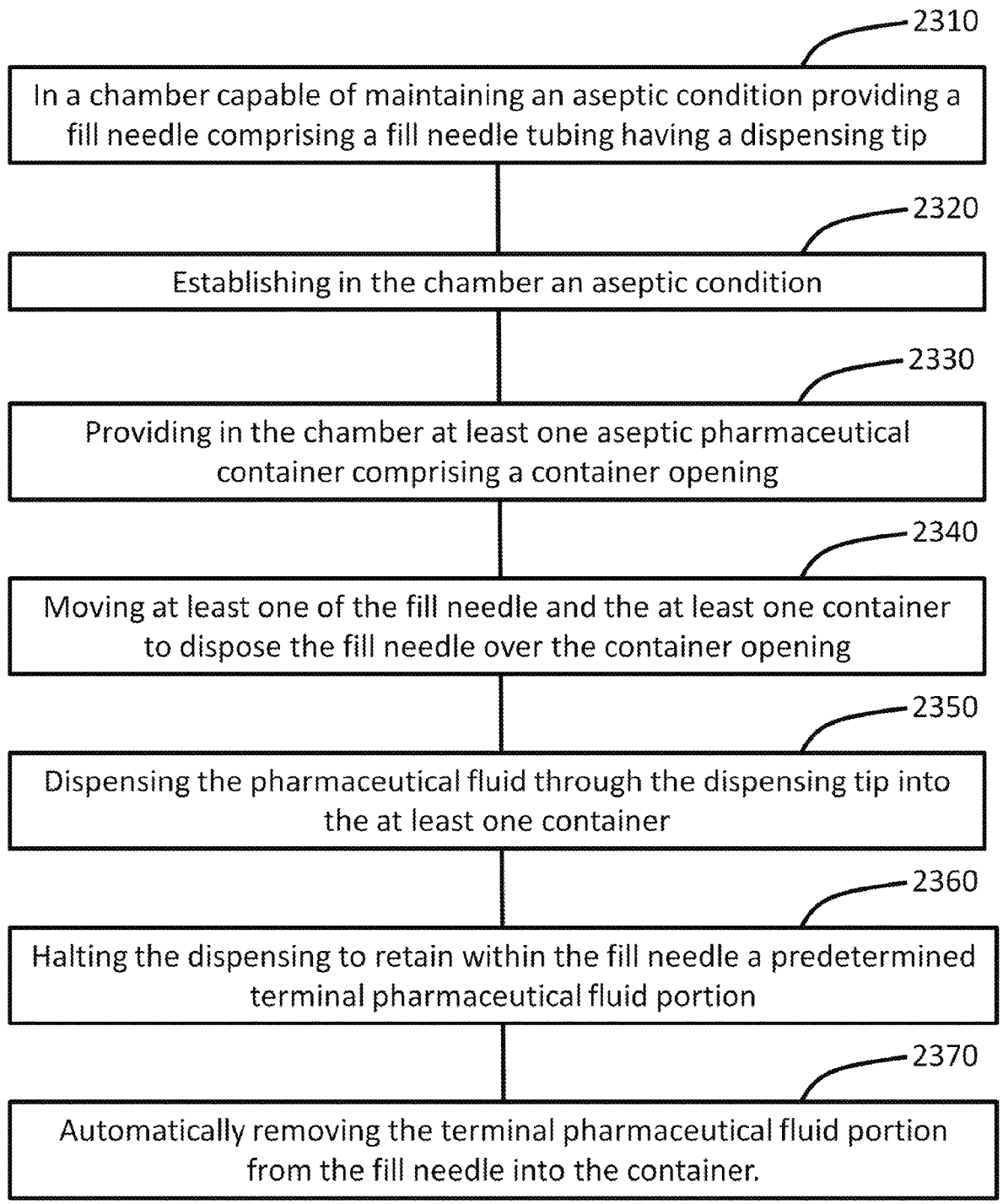
FIG. 23 is a drawing of a flow chart for a method of aseptically filling a pharmaceutical container with a pharmaceutical fluid in a chamber capable of maintaining an aseptic condition.

In another aspect, described at the hand of the flow chart shown in FIG. 23, a method is provided for aseptically filling pharmaceutical container 411 with pharmaceutical fluid 702 using the purgeable fill needle of FIG. 17, FIG. 18, FIG. 19, or FIG. 20, the method comprising: in a chamber 420 (See FIG. 1) capable of maintaining an aseptic condition providing [2310] a fill needle comprising fill needle tubing 501a, 501b, 501c, 501d, 501e, 501f having dispensing tip 506a, 506b, 506c, 506d, 506e, 506f; Establishing [2320] in the chamber 420 an aseptic condition; providing [2330] in the chamber 420 at least one aseptic pharmaceutical container 411 comprising a container opening; moving [2340] at least one of the fill needle and the at least one container to dispose the fill needle over the container opening; dispensing pharmaceutical fluid 702 through dispensing tip 506a, 506b, 506c, 506d, 506e, 506f and the container opening into the at least one container 411; halting [2360] dispensing to retain within the fill needle a terminal pharmaceutical fluid portion 704a, 704b, 704c, 704d, 704e, 704f; and automatically removing [2370] terminal pharmaceutical fluid portion 704a, 704b, 704c, 704d, 704e, 704f from the fill needle into the container after halting [2360] dispensing. The method may further comprise providing a controller, for example controller 440 of FIG. 1. Removing [2370] may be automatically initiated and terminated by controller 440.

As per the systems of FIG. 17 and FIG. 18, automatically removing terminal pharmaceutical fluid portion 704a, 704b may comprise injecting aseptic gas into fill needle tubing 501a, 501b. Providing the fill needle may comprise providing a fill needle having gas inlet orifice 509A, 509B in fill needle tubing 501a, 501b proximate dispensing tip 506a, 506b; and injecting aseptic gas into fill needle tubing 501a, 501b may comprise injecting aseptic gas via orifice 509A, 509B. The method may comprise maintaining a flow of gas until no more pharmaceutical fluid 702 is removed from the fill needle. In another embodiment, as per FIG. 19, automatically removing [2370] terminal pharmaceutical fluid portion 704c may comprise inflating bladder 511 within dispensing tip 506c.

Injecting aseptic gas may comprise injecting aseptic nitrogen gas, aseptic air, or aseptic helium gas. Injecting aseptic gas may comprise filtering gas to render it aseptic. Injecting aseptic gas may comprise operating a gas valve, for example valve 466 of FIG. 17 and FIG. 18. Operating gas valve 466 may comprise automatically controlling valve 466 by means of controller 440 of FIG. 1 via valve control line 452.

Providing [2310] the fill needle may comprise, as per FIG. 20, providing flexible terminal tube 515 disposed within dispensing tip 506d and compression actuator 513 disposed to compress flexible terminal tube 515; and automatically removing [2370] terminal pharmaceutical fluid portion 704d may comprise automatically operating compression actuator 513 to compress flexible terminal tube 515. Operating actuator 513 may comprise piezoelectrically actuating the actuator or electromechanically actuating actuator 513.

Providing [2310] the fill needle may comprise providing the fill needle tubing with a vibration actuator disposed on the fill needle tubing for shaking the dispensing tip and automatically removing [2370] the terminal pharmaceutical fluid portion comprises automatically operating the vibration actuator to shake the dispensing tip.

Providing [2310] the fill needle may comprise providing a fill needle having a gas channel surrounding the fill needle tubing, the gas channel having an annular opening with respect to and proximate to the dispensing tip; and automatically removing [2370] the terminal pharmaceutical fluid portion may comprise annularly blowing an aseptic gas at the terminal pharmaceutical fluid portion through the annular opening.

Providing [2310] the fill needle may comprise providing a first robotic arm, for example robotic arm 415 of FIG. 1, having a first end effector, for example end effector 1100 of FIG. 14B; and moving the fill needle may comprise engaging the fill needle with the first end effector 1100 and operating the robotic arm 415. Providing a first robotic arm may comprise providing first articulated robotic arm 415.

Providing [2330] at least one container 411 may comprise providing a container nest bearing at least one container 411. Providing the container nest may further comprise providing a second robotic arm having a second end effector; and moving the at least one container may comprises engaging the container nest with the second end effector and operating the second robotic arm. Providing the second robotic arm may comprise providing a second articulated robotic arm. FIG. 9 of U.S. patent application Ser. No. 15/729,655, herein incorporated in full, shows containers 510 in a nest 500 and nest 500 is moved by an articulated robotic arm 800, which serves as second robotic arm in the present specification. In another embodiment, providing the container nest may comprise providing the container nest held in a locating structure of a rotary stage, and moving the at least one container may comprise rotating the rotary stage. Suitable rotary stages for holding and moving nests of containers are described in detail in United States Patent Publications US 2018-0072446 A1 (published Mar. 15, 2018), US 2018-0071168 A1 (published Mar. 15, 2018), and US 2018-0282008 A1 (published Oct. 4, 2018), and PCT International Patent Publication WO/2018/049516 (published Mar. 22, 2018), all of which are herein incorporated in full.

Providing [2310] the fill needle may comprise providing the fill needle closed with a fill needle sheath, for example fill needle sheath, for example sheath 503' of FIG. 9A; sterilizing chamber 420 to establish within chamber 420 an aseptic condition; and disengaging and removing the fill needle from fill needle sheath 503'. The method may further comprise engaging the fill needle with fill needle sheath 503' after removing terminal pharmaceutical fluid portion 704a, 704b, 704c, 704d, 704e, 704f from the fill needle.

Figure 24:
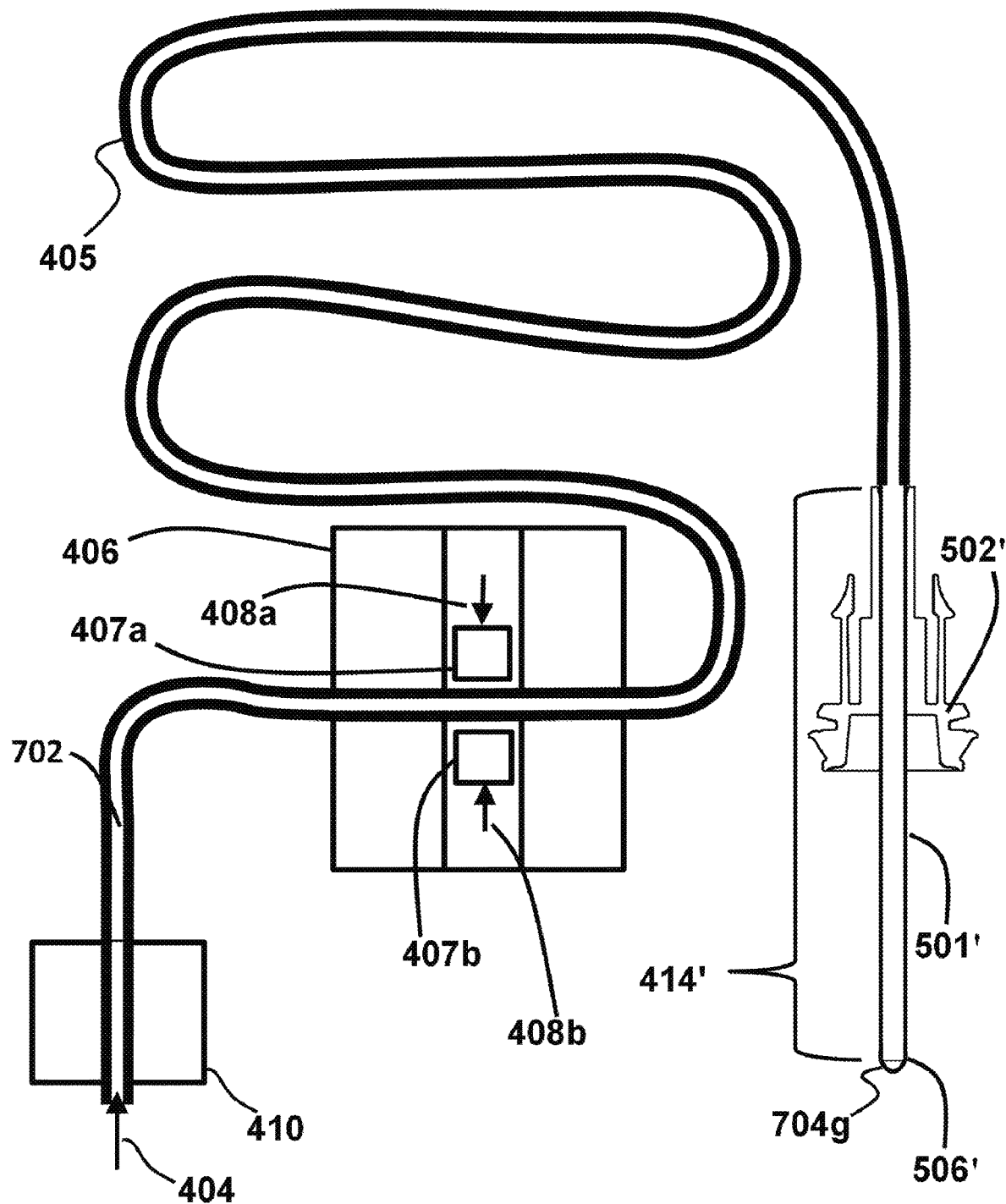
FIG. 24 shows an implementation of a fill needle system employing a fluid pulse induction system to dislodge droplets of fluid from a dispensing tip of a fill needle.

FIG. 24 shows an implementation of a fill needle system employing, by way of example, fill needle 414' of aseptically sealed fill needle package 900 shown in FIGS. 9A, 9B and 9C. Fill needle 414' comprises fill needle tubing 501' and fill needle hub 502'. Fill needle tubing 501' is in fluid communication with pharmaceutical fluid source, for example container 401 of FIG. 1, via flexible tubing 405 and extending through fill needle hub 502', fill needle 414' having fill needle dispensing tip 506' disposed at a dispensing end of fill needle tubing 405. Any other fill needle suitable for filling containers with pharmaceutical fluid 702 may be employed, including fill needle 414 of FIG. 1 and FIG. 2. As already described at the hand of FIG. 1, flexible tubing 405 enters chamber 420 via an aseptically sealing flange (not shown), so that the exterior of fluid path 404 within chamber 420 is aseptically sealed with respect to the interior of chamber 420. Pump 410 urges the fluid in question along fluid path 404 within flexible tubing 405. None of the elements of FIG. 24 is drawn to scale.

Fluid pressure pulse induction system 406, shown schematically in FIG. 24, is disposed along fluid path 404 and arranged and configured to induce a fluid pressure pulse in the fluid within flexible tubing 405 at the end of a filling cycle. This fluid pressure pulse ensures that any droplet of fluid 704g remaining at the tip of fill needle tubing 501' at the end of a filling cycle is ejected into a container being filled with the fluid provided by pump 410 along fluid path 404 through flexible tubing 405. By suitable adjustment of pressure pulse induction system 406, the fluid pressure pulse may be calibrated and set to dislodge only fluid droplet 704g and no further droplets of fluid.

Different embodiments of fluid pressure pulse induction system 406 are contemplated. In FIG. 24, two pressure members 407a and 407b are shown. These two pressure members may be actuated by different means to move as indicated by arrows 408a and 408b respectively, as indicated in FIG. 24. In other embodiments, one of member 407a and member 407b may be stationary, and the other of member 407a and member 407b may move as indicated when actuated. In either of these embodiments, flexible tubing 405 is compressed between pressure members 407a and 407b to induce a fluid pressure pulse in the fluid within flexible tubing 405. Any one or more of the force on members 407a and 407b; the duration of the pressure pulse; the length of tubing 405 compressed; the geometrical shapes pressure members 407a and 407b; and the angle at which members 407a and 407b close tubing 405 may be adapted to produce a desired amplitude and duration of pulse.

Actuation of pressure members 407a and/or 407b may be by electro-mechanical means, by pneumatic means, by magnetic induction transducer, piezoelectric transducer or any other means that will compress flexible tubing 405 in a controllable, repeatable and calibratable fashion. Any of the fluid pressure pulse induction systems 406 described herein may be controlled by controller 440 of FIG. 1. Controller 440 may be preprogrammed to produce via fluid pressure pulse induction system 406 a predetermined fluid pressure pulse amplitude and duration within fill needle tubing 501'. The predetermined fluid pressure pulse amplitude and duration within fill needle tubing 501' may be selected to specifically dislodge only a single droplet 704 of pharmaceutical fluid retained on dispensing tip 506' after halting the dispensing.

Figure 25:
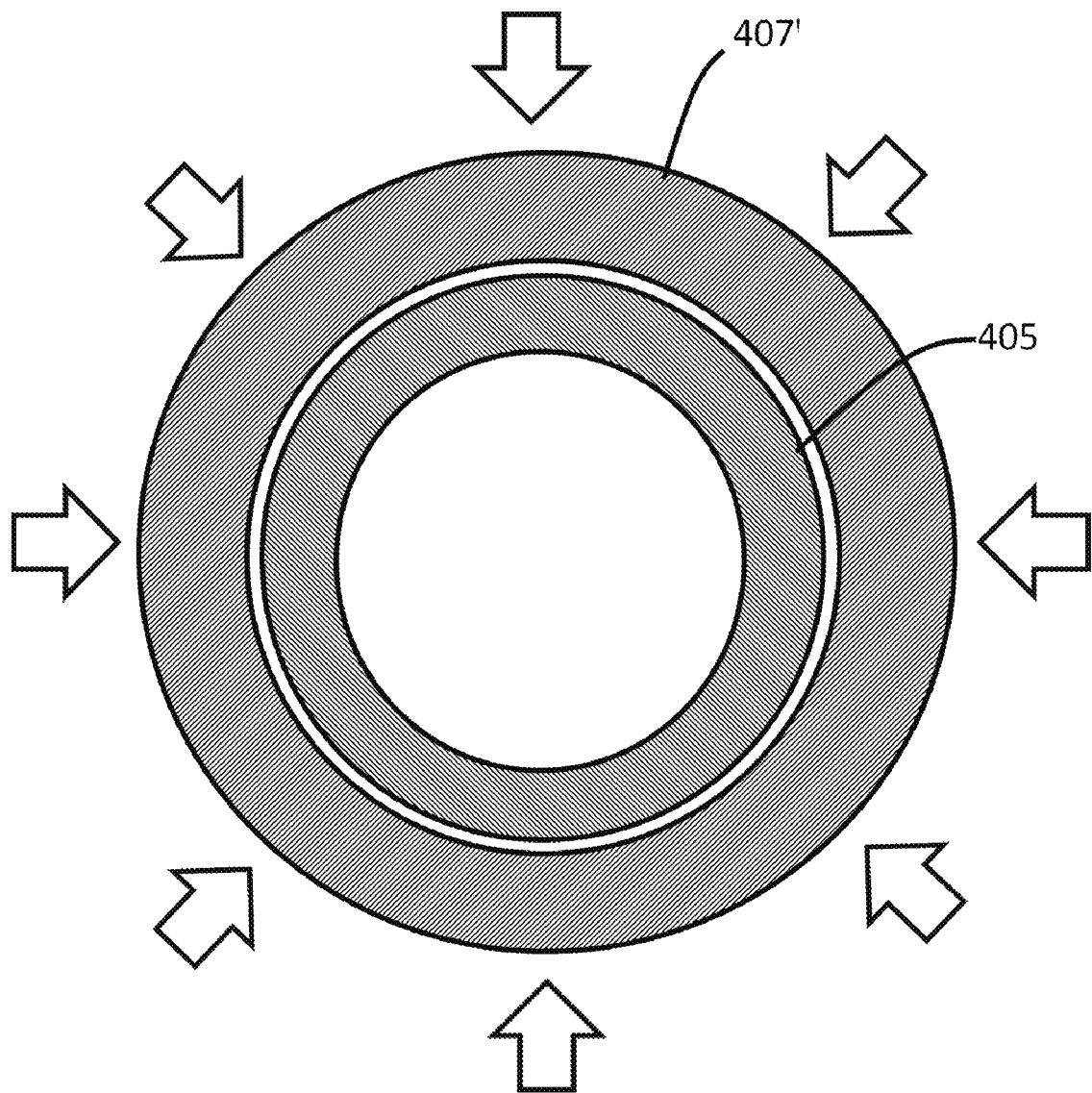
FIG. 25 shows an implementation of a fluid pulse induction system.

In other embodiments of fluid pressure pulse induction system 406, more than two pressure members may be employed to compress flexible tubing 405. In yet further embodiments of fluid pressure pulse induction system 406, a pressure member may be arranged to contract annularly around flexible tubing 405. To this end, as shown in FIG. 25, flexible tubing 405 may be routed through a piezoelectrically activated tube 407'. Application of an actuating voltage to piezoelectrically activated tube 407' causes tube 407' to contract annularly, as shown by the arrows, thereby inducing a fluid pressure pulse in flexible tubing 405.

Fluid pressure pulse induction system 406 may be disposed along fluid path 404 outside chamber 420 in order to minimize the number of moving parts inside chamber 420 that may potentially contribute to dust and debris creation in chamber 420.

Figure 26:
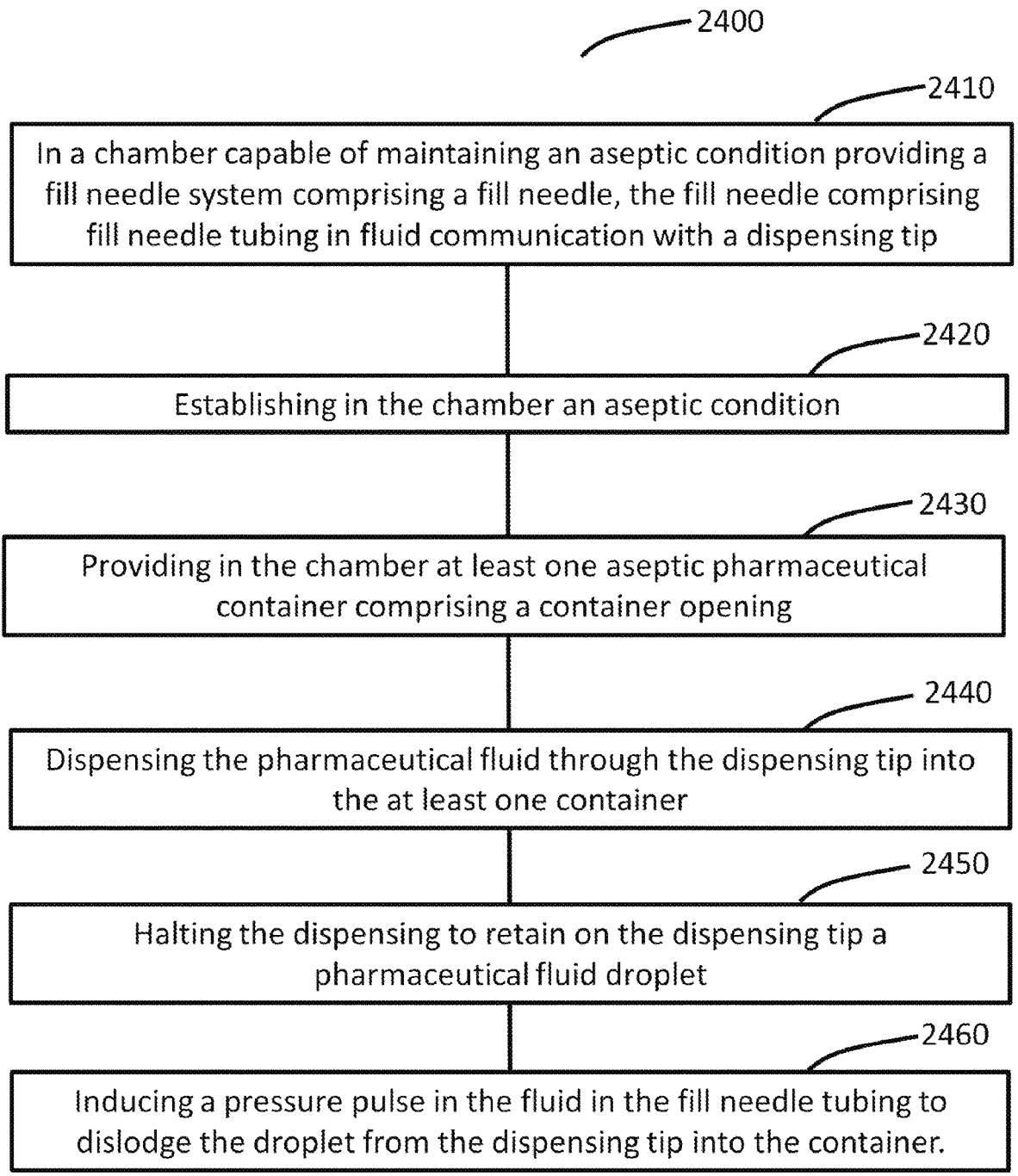
FIG. 26 is a drawing of a flow chart for another method of aseptically filling a pharmaceutical container with a pharmaceutical fluid in a chamber capable of maintaining an aseptic condition.

In another aspect, described at the hand of the flow chart shown in FIG. 26, method 2400 is provided for aseptically filling pharmaceutical container 411 with pharmaceutical fluid 702 using the fill needle system of FIG. 24, the method comprising: in chamber 420 (See FIG. 1) capable of maintaining an aseptic condition providing [2410] a fill needle system comprising fill needle 414', fill needle 414' comprising fill needle tubing 501' in fluid communication with dispensing tip 506'; establishing [2420] in chamber 420 an aseptic condition; providing [2430] in chamber 420 at least one aseptic pharmaceutical container 411 comprising a container opening; dispensing [2440] pharmaceutical fluid 702 through dispensing tip 506' and the container opening into the at least one container 411; halting [2450] dispensing to retain on dispensing tip 506' pharmaceutical fluid droplet 704g; and inducing [2460] a pressure pulse in fluid 702 in fill needle tubing 501' to dislodge droplet 704g from dispensing tip 506 into container 411. The method may further comprise providing a controller, for example controller 440 of FIG. 1. Halting [2450] dispensing and inducing [2460] a pressure pulse may be automatically controlled by controller 440.

Providing [2410] the fill needle system may comprise providing a fluid pressure pulse induction system 406 and flexible tubing 405 in fluid communication with fill needle tubing 501' and dispensing tip 506', wherein the pressure pulse induction system 406 is disposed and configured to compress flexible tubing 405. Inducing [2460] a pressure pulse in fluid 702 may comprise operating fluid pressure pulse induction system 406 to compress flexible tubing 405. Compressing flexible tubing 405 may comprise annularly compressing flexible tubing 405.

Dispensing [2440] pharmaceutical fluid 702 may comprise moving at least one of fill needle 414' and the at least one container 411 to dispose fill needle 414' over the container opening.

Providing [2410] the fill needle system may further comprise providing a first robotic arm, for example robotic arm 415 of FIG. 1, having a first end effector, for example end effector 1100 of FIG. 14B. Moving fill needle 14' may comprise engaging fill needle 414' with first end effector 1100 and operating robotic arm 415. Providing a first robotic arm may comprise providing first articulated robotic arm 415.

Providing [2430] at least one container 411 may comprise providing a container nest bearing the at least one container 411. Providing the container nest may further comprise providing a second robotic arm having a second end effector; and moving the at least one container 411 may comprise engaging the container nest with the second end effector and operating the second robotic arm. Providing the second robotic arm may comprise providing a second articulated robotic arm. FIG. 9 of United States Patent Publication US 2018-0282008 A1, herein incorporated in full, shows containers 510 in a nest 500 and nest 500 is moved by an articulated robotic arm 800, which serves as second robotic arm in the present specification. In another embodiment, providing the container nest may comprise providing the container nest held in a locating structure of a rotary stage, and moving the at least one container may comprise rotating the rotary stage. Suitable rotary stages for holding and moving nests of containers are described in detail in United States Patent Publications US 2018-0072446 A1 (published Mar. 15, 2018), US 2018-0071168 A1 (published Mar. 15, 2018), and US 2018-0282008 A1 (published Oct. 4, 2018), and PCT International Patent Publication WO/2018/049516 (published Mar. 22, 2018), all of which are herein incorporated in full.

Providing [2410] the fill needle may comprise providing the fill needle closed with a fill needle sheath, for example fill needle sheath 503' of FIG. 9A; sterilizing chamber 420 to establish within chamber 420 an aseptic condition; and disengaging and removing fill needle 414' from fill needle sheath 503'. The method may further comprise engaging fill needle 414' with fill needle sheath 503' after automatically dislodging pharmaceutical fluid droplet 704g from fill needle 414' into container 411.

Additional Notes

The above detailed description includes references to the accompanying drawings, which form a part of the detailed description. The drawings show, by way of illustration, specific embodiments in which the invention may be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a tangible computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A fill needle system for aseptically dispensing a pharmaceutical fluid in a chamber capable of maintaining an aseptic condition, the system comprising:
   a fill needle hub,
   a fill needle tubing in fluid communication with a pharmaceutical fluid source via flexible tubing and extending through the fill needle hub;
   a fill needle dispensing tip disposed at a dispensing end of the fill needle tubing;
   a fill needle sheath shaped and arranged to removably mate with and seal aseptically to the fill needle hub to form an aseptically sealed volume enclosing the dispensing tip; and
   a fluid pressure pulse induction system disposed and configured to compress the flexible tubing.

2. The system of claim 1, further comprising a controller configured to control the dispensing of the pharmaceutical fluid via the dispensing tip.

3. The system of claim 2, wherein the controller is configured to operate the fluid pressure pulse induction system to automatically compress the flexible tubing after halting dispensing of the pharmaceutical fluid.

4. The system of claim 2, wherein the controller is configured to induce in the fill needle tubing a pressure pulse of predetermined fluid amplitude and duration.

5. The system of claim 1, wherein the fluid pressure pulse induction system is disposed and configured to annularly compress the flexible tubing.

6. The system of claim 1, wherein the fluid pressure pulse induction system is one of piezoelectrically actuated, electromechanically actuated, magnetically actuated, and pneumatically actuated.

7. The system of claim 1, wherein the fill needle dispensing tip includes a vibration actuator.

8. The system of claim 7, wherein the fill needle dispensing tip includes hydrophobic material proximate the vibration actuator.

9. The system of claim 7, wherein the vibration actuator is disposed to vibrate the fill needle tubing.

10. The system of claim 7, wherein the fill needle dispensing tip includes hydrophobic material.

11. The system of claim 7, wherein the fill needle tubing includes hydrophobic material proximate the vibration actuator.

12. The system of claim 7, wherein the vibration actuator is configured to be actuated electromechanically.

13. The system of claim 7, wherein the vibration actuator is configured to be actuated piexolectrically.

14. The system of claim 1, wherein the fill needle dispensing tip includes a gas injector.

15. The system of claim 14, wherein the fill needle dispensing tip includes hydrophobic material proximate the gas injector.

16. The system of claim 1, wherein the fill needle dispensing tip includes a mechanism for squeezing the fill needle tubing.

17. The fill needle of claim 16, wherein the fill needle dispensing tip further includes a bladder.

18. The system of claim 17, wherein the fill needle dispensing tip injects gas into the bladder.

19. The system of claim 18, wherein the bladder is disposed around the fill needle tubing proximate the fill needle dispensing tip.

20. The system of claim 1, wherein the fill needle dispensing tip includes a levered piezoelectric actuator.

21. The system of claim 20, wherein the fill needle dispensing tip includes a bladder, and the levered piezoelectric actuator is disposed to compress the bladder upon actuation.

* * * * *